(12) United States Patent
Cogan et al.

(10) Patent No.: US 7,790,712 B2
(45) Date of Patent: Sep. 7, 2010

(54) SUBSTITUTED [1,4]DIAZEPINO[1,2-A]INDOLES AND AZEPINO[1,2-A]INDOLES AS ANTI-CYTOKINE INHIBITORS

(75) Inventors: Derek Cogan, Sandy Hook, CT (US); Donghong A. Gao, Hopewell Junction, NY (US); Daniel R. Goldberg, Redding, CT (US); Craig Andrew Miller, Mt. Vernon, NY (US); Neil Moss, Ridgefield, CT (US); Matthew Russell Netherton, Danbury, CT (US); Philip Dean Ramsden, Mt. Vernon, NY (US); Zhaoming Xiong, Brookfield, CT (US)

(73) Assignee: Boehringer Ingelheim Pharmaceutical, Inc., Ridgefield, CT (US)

( * ) Notice: Subject to any disclaimer, the term of this patent is extended or adjusted under 35 U.S.C. 154(b) by 857 days.

(21) Appl. No.: 11/276,935

(22) Filed: Mar. 17, 2006

(65) Prior Publication Data

US 2006/0276453 A1 Dec. 7, 2006

Related U.S. Application Data

(60) Provisional application No. 60/719,017, filed on Sep. 21, 2005, provisional application No. 60/662,567, filed on Mar. 17, 2005.

(51) Int. Cl.
C07D 487/04 (2006.01)
A61K 31/519 (2006.01)
C07D 471/04 (2006.01)
A61K 31/4985 (2006.01)
A61K 31/5365 (2006.01)
A61P 37/06 (2006.01)

(52) U.S. Cl. .................. 514/220; 514/214.01; 514/250; 514/294; 540/496; 540/522; 540/558; 546/94; 544/344

(58) Field of Classification Search ............ 514/214.01, 514/220, 250, 294; 540/496, 522, 558; 544/344; 546/94
See application file for complete search history.

(56) References Cited

U.S. PATENT DOCUMENTS 7,348,425 B2 * 3/2008 Hudyma et al. ............. 540/576
2006/0276496 A1 12/2006 Goldberg et al.

FOREIGN PATENT DOCUMENTS

WO 02/10169 A1 2/2002

WO 2008/098096 A1 8/2008

OTHER PUBLICATIONS

Anderson et al, "Pyrrolopyridine Inhibitors of Mitogen-Activated Protein Kinase-Activated Protein Kinase 2 (MK-2)" Journal of Medicinal Chemistry, vol. 50, pp. 2647-2654 (2007).*
Scheiven, G. "The Biology of p38 Kinase: A Central Role in Inflammation" Current Topics in Medicinal Chemistry, vol. 5, pp. 921-928 (2005).*
Goldberg, D. R., et al., "Pyrazinoindolone inhibitors of MAPKAP—K2," Bioorganic & Medicinal Chemistry Letters (2008), 18(3), 938-941.
Schlapbach, Achim et al., "Pyrrolo-pyrimidones: A novel class of MK2 inhibitors with potent cellular activity," Bioorganic & Medicinal Chemistry Letters (2008), 18(23), 6142-6146.
Wu, Jiang-Ping, et al., "The discovery of carboline analogs as potent MAPKAP—K2 inhibitors," Bioorganic & Medicinal Chemistry Letters (2007), 17(16), 4664-4669.
Xiong, Zhaoming et al., "Synthesis and SAR studies of indole-based MK2 inhibitors," Bioorganic & Medicinal Chemistry Letters (2008), 18(6), 1994-1999.
Hendi, Shivakumar B., et al; Synthesis of II-Methyl-2,3,4,5-tetrahydro-IH-[1,4]diazepino[I,2a]indoles & I-(3-Aminopropyl)-2-hydroxymethyl-3-methylindoles; Indian Journal of Chemistry (1981) vol. 20B pp. 288-289.
Rajur, Sharanabasava, B., et al; Synthesis of II-phenyl-2,3,4,5-tetrahydro-1 H-(1,4)diazepino(1,2-a)indoles and 1-(3-Aminopropyl)-2-hydroxymethyl-3-phenylindoles as 5-Hydroxytryptamine Antagonists; Journal of Pharmaceutical Sciences (1990) vol. 79, No. 2, pp. 168-172.

* cited by examiner

*Primary Examiner*—James O Wilson
*Assistant Examiner*—Susanna Moore
(74) *Attorney, Agent, or Firm*—Michael P. Morris; Mary-Ellen M. Devlin; Edward S. Lazer

(57) ABSTRACT

The application relates to compounds of formula Ia

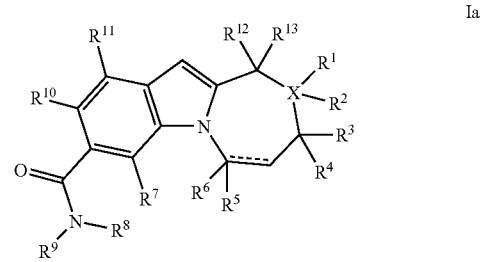

and analogues thereof wherein $R^1$ to $R^{13}$ and X are as defined herein. The invention also relates to the use of the compounds of formula Ia as inhibitors of Mitogen-Activated Protein Kinase-Activated Protein kinase-2 (MAPKAP-k2), and also to a method for preventing or treating a disease or disorder that can be treated or prevented by modulating the activity of MAPKAP-K2 in a subject and to pharmaceutical compositions and kits that include these MAPKAP-K2 inhibitors.

5 Claims, No Drawings

SUBSTITUTED [1,4]DIAZEPINO[1,2-A]INDOLES AND AZEPINO[1,2-A]INDOLES AS ANTI-CYTOKINE INHIBITORS

PRIORITY

The present application claims priority under 35 U.S.C. 119(e) to U.S. Provisional Patent Applications No.: 60/719,017, filed Sep. 21, 2005, and 60/662,567, filed Mar. 17, 2005, the entire contents of which are incorporated herein by reference.

BACKGROUND OF THE INVENTION

1. Field of the Invention

This present invention relates to heterocyclic compounds and analogues thereof and their use as inhibitors of Mitogen-Activated Protein Kinase-Activated Protein kinase-2 (MAP-KAP-k2), and also to a method for preventing or treating a disease or disorder that can be treated or prevented by modulating the activity of MAPKAP-K2 in a subject and to pharmaceutical compositions and kits that include these MAP-KAP-K2 inhibitors.

2. Description of Related Art

Mitogen Activated Protein Kinases (MAPKs) are members of signal transduction pathways that change cell physiology in response to external stimuli by activating a variety of downstream signaling genes products. These gene products control diverse cellular functions such as the production of pro-inflammatory cytokines involved in establishing and maintaining specific human diseases. The MAPKs are activated by phosphorylation on specific residues within the activation loop sequence by specific upstream MAPK kinases (MKKs) in response to a cellular activation signal. In turn, the MAPKs activate a variety of downstream gene products. There are four major classes of MAPKs: 1) the archetypal Extracellular Regulated kinases (ERKs), 2) the c-jun N-terminal kinases (JNKs), 3) the p38 MAPKs and finally, 4) the ERK5 or BigMAPKs. The MAPK pathways are involved in alterations in cell physiology resulting from cell stimulation. They control various cell processes such as: cell death, cell cycle machinery, gene transcription and protein translation, (Tibbles and Woodgett;Kyriakis and Avruch).

Of particular relevance to this invention, is the p38 MAPK family (also known as p38, SAPK2a, RK, MPK2, Mxi2 and CSBP). These kinases, most notably the p38alpha and p38beta isoforms, can activate a wide variety of regulatory proteins. In this manner, p38 can diversify downstream signaling leading to a wide variety of cellular outcomes. Central to the signal transduction process initiated by p38 activation is MAPKAP-K2. Most of the physiological outcomes of MAPKAP-K2 have been established using mice genetically deficient in MAPKAP-K2 (designated MAPKAP-K2$^{(-/-)}$). A significant phenotype of the MAPKAP-K2$^{(-/-)}$mice is that pro-inflammatory cytokine production is inhibited following stimulation of splenocytes with lipopolysaccharide (LPS). Specifically, the production of tumor necrosis factor-alpha (TNF-alpha) is blocked by 92%, interleukin-1beta (IL-1-beta) is blocked by 40%, IL-6 is blocked by 87% and interferon-gamma (IFN-gamma) is blocked by 86%. This phenotype cannot be rescued by the expression of a kinase dead MAPKAP-K2 mutant, indicating that the kinase function of MAPKAP-K2 is required for proinflammatory cytokine production (Kotlyarov et al.). Thus, an inhibitor of MAPKAP-K2 kinase activity has the potential to exhibit the same inhibitory effects on the production of proinflammatory cytokines.

MK2 activates a number of substrates, including the mRNA binding protein, tristetraproline (TTP). TTP expression is induced by proinflammatory stimuli such as lipopolysaccharide (LPS) or tumor necrosis factor-alpha (TNF-alpha). TTP binds to the AU-rich element within the 3'-untranslated region of the TNF-alpha transcript resulting in a decrease in TNF-alpha mRNA stability (Phillips et al.). TTP$^{(-/-)}$ mice exhibit many defects including arthritis and systemic lupus erythematosis-like symptoms presumably resulting from an increase in circulating TNF-alpha levels (Taylor et al.). Data from in vivo studies with MK2$^{(-/-)}$ indicate that the repressive effects of TTP on both TNF-alpha and interleukin-6 (IL-6) production are downstream of MK2 further establishing p38-MK2-TTP as a critical signaling sequence for the production of proinflammatory cytokines (Neininger et al.).

Elevated levels of proinflammatory cytokines are associated with a number of diseases such as toxic shock syndrome, rheumatoid arthritis, osteoarthritis, diabetes and inflammatory bowel disease (Dinarello). In these diseases, chronic elevation of inflammation exacerbates or causes much of the pathophysiology observed. For example, rheumatoid synovial tissue becomes invaded with inflammatory cells that result in destruction to cartilage and bone (Koch, Kunkel, and Strieter). Studies suggest that inflammatory changes mediated by cytokines may be involved in endothelial cell pathogenesis including restenosis after percutaneous transluminal coronary angioplasty (PTCA) (Tashiro et al.). An important and accepted therapeutic approach for potential drug intervention in these diseases is the reduction of pro-inflammatory cytokines such as TNF-alpha and IL-1-beta. Several biological agents directed against these pro-inflammatory cytokines (anti-TNF antibodies, a soluble TNF receptor and an IL-1 receptor antagonist) have been FDA approved for the treatment of RA, Crohn's disease and psoriatic arthritis (Rankin et al.; Stack et al.; Present et al.; Rutgeerts; Abbott Laboratories markets HUMIRA® (Adalimumab) for the treatment of rheumatoid arthritis (RA); Weinblatt et al.; Jarvis and Faulds; Mease et al.; Nuki et al.).

A soluble TNF-alpha receptor has been engineered that interacts with TNF-alpha. The approach is similar to that described above for the monoclonal antibodies directed against TNF-alpha; both agents bind to soluble TNF-alpha, thus reducing its concentration. One version of this construct, Enbrel® (Immunex, Seattle, Wash.), is marketed for the treatment of rheumatoid arthritis, psoriasis, ankylosing spondylitis, and psoriatic arthritis. Another version of the TNF-alpha receptor, Ro 45-2081 (Hoffman-LaRoche Inc., Nutley, N.J.) has demonstrated efficacy in various animal models of allergic lung inflammation and acute lung injury. Ro 45-2081 is a recombinant chimeric molecule constructed from the soluble 55 kDa human TNF receptor fused to the hinge region of the heavy chain IgG1 gene and expressed in eukaryotic cells (Renzetti and Gater).

Proinflammatory cytokines such as TNF-alpha and IL-6 are also important mediators of septic shock and associated cardiopulmonary dysfunction, acute respiratory distress syndrome (ARDS) and multiple organ failure. In a study of patients presenting with sepsis, a correlation was found between TNF-alpha and IL-6 levels and septic complications (Terregino et al.). TNFα has also been implicated in cachexia and muscle degradation, associated with HIV infection (Lahdevirta et al.). Obesity is associated with an increase incidence of infection, diabetes and cardiovascular disease. Abnormalities in TNF-alpha expression have been noted for each of the above conditions (Loffreda et al.). It has been proposed that elevated levels of TNF-alpha are involved in other eating related disorders such as anorexia and bulimia nervosa. Pathophysiological parallels are drawn between anorexia nervosa and cancer cachexia (Holden and Pakula). An inhibitor of TNF-alpha production, HU-211, was shown to improve the outcome of closed brain injury in an experimental model (Shohami et al.). Atherosclerosis is known to have an inflammatory component and cytokines such as IL-1 and TNF have been suggested to promote the disease. In an animal model an IL-1 receptor antagonist was shown to inhibit fatty streak formation (Elhage et al.).

TNF-alpha levels are elevated in airways of patients with chronic obstructive pulmonary disease and it may contribute to the pathogenesis of this disease (Higham et al.).

Circulating TNFα may also contribute to weight loss associated with this disease (Takabatake et al.). Elevated TNF-alpha levels have also been found to be associated with congestive heart failure and the level has been correlated with severity of the disease (Feldman et al.). In addition, TNF-alpha has been implicated in reperfusion injury in lung (Borjesson et al.), kidney (Lemay et al.), and the nervous system (Mitsui et al.). TNF-alpha is also a potent osteoclastogenic agent and is involved in bone resorption and diseases involving bone resorption (bu-Amer et al.). It has also been found highly expressed in chondrocytes of patients with traumatic arthritis (Melchiorri et al.). TNF-alpha has also been shown to play a key role in the development of glomerulonephritis (Le et al.).

The proinflammatory cytokine IL-6 has been implicated with the acute phase response. IL-6 is a growth factor in a number in oncological diseases including multiple myeloma and related plasma cell dyscrasias (Treon and Anderson). It has also been shown to be an important mediator of inflammation within the central nervous system. Elevated levels of IL-6 are found in several neurological disorders including AIDS dementia complex, Alzheimer's disease, multiple sclerosis, systemic lupus erythematosus, CNS trauma and viral and bacterial meningitis (Gruol and Nelson). IL-6 also plays a significant role in osteoporosis. In murine models it has been shown to effect bone resorption and to induce osteoclast activity (Ershler, Harman, and Keller). Marked cytokine differences, such as IL-6 levels, exist in vivo between osteoclasts of normal bone and bone from patients with Paget's disease (Mills and Frausto). A number of cytokines have been shown to be involved in cancer cachexia. The severity of key parameters of cachexia can be reduced by treatment with anti IL-6 antibodies or with IL-6 receptor antagonists (Strassmann and Kambayashi). Several infectious diseases, such as influenza, indicate IL-6 and IFN alpha as key factors in both symptom formation and in host defense (Hayden et al.). Overexpression of IL-6 has been implicated in the pathology of a number of diseases including multiple myeloma, rheumatoid arthritis, Castleman's disease, psoriasis, post-menopausal osteoporosis and juvenile idiopathic arthritis (Simpson et al.; Nishimoto and Kishimoto). Compounds that interfered with the production of cytokines including IL-6, and TNF were effective in blocking a passive cutaneous anaphylaxis in mice (Scholz et al.). More recently, a humanized antibody directed against the IL-6 receptor, demonstrated efficacy in a randomized double-blind pilot human clinical study by significantly reducing the Crohn's disease activity index (Ito et al.).

IFN-gamma has been implicated in a number of diseases. It has been associated with increased collagen deposition that is a central histopathological feature of graft-versus-host disease (Parkman). Following kidney transplantation, a patient was diagnosed with acute myelogenous leukemia. Retrospective analysis of peripheral blood cytokines revealed elevated levels of GM-CSF and IFN-gamma. These elevated levels coincided with a rise in peripheral blood white cell count (Burke et al.). The development of insulin-dependent diabetes (Type 1) can be correlated with the accumulation in pancreatic islet cells of T-cells producing IFN-gamma (Ablamunits et al.). IFN-gamma along with TNF, IL-2 and IL-6 lead to the activation of most peripheral T-cells prior to the development of lesions in the central nervous system for diseases such as multiple sclerosis (MS) and AIDS dementia complex (Martino et al.). Atherosclerotic lesions result in arterial disease that can lead to cardiac and cerebral infarction. Many activated immune cells are present in these lesions, mainly T-cells and macrophages. These cells produce large amounts of proinflammatory cytokines such as TNF, IL-1 and IFN-gamma. These cytokines are thought to be involved in promoting apoptosis or programmed cell death of the surrounding vascular smooth muscle cells resulting in the atherosclerotic lesions (Geng). Allergic subjects produce mRNA specific for IFN-gamma following challenge with Vespula venom (Bonay et al.). The expression of a number of cytokines, including IFN-gamma has been shown to increase following a delayed type hypersensitivity reaction thus indicating a role for IFN-gamma in atopic dermatitis (Szepietowski et al.). Histopathologic and immunohistologic studies were performed in cases of fatal cerebral malaria. Evidence for elevated IFN-gamma amongst other cytokines was observed indicating a role in this disease (Udomsangpetch et al.). The importance of free radical species in the pathogenesis of various infectious diseases has been established. The nitric oxide synthesis pathway is activated in response to infection with certain viruses via the induction of proinflammatory cytokines such as IFN-gamma (Akaike, Suga, and Maeda). Patients, chronically infected with hepatitis B virus (HBV) can develop cirrhosis and hepatocellular carcinoma. Viral gene expression and replication in HBV transgenic mice can be suppressed by a post-transcriptional mechanism mediated by IFN-gamma, TNF and IL-2 (Chisari and Ferrari). IFN-gamma can selectively inhibit cytokine induced bone resorption. It appears to do this via the intermediacy of nitric oxide (NO) which is an important regulatory molecule in bone remodeling. NO may be involved as a mediator of bone disease for such diseases as: rheumatoid arthritis, tumor associated osteolysis and postmenopausal osteoporosis (Evans and Ralston). Studies with gene deficient mice have demonstrated that the IL-12 dependent production of IFN-gamma is critical in the control of early parasitic growth. Although this process is independent of nitric oxide the control of chronic infection does appear to be NO dependent (Alexander et al.). NO is an important vasodilator and convincing evidence exists for its role in cardiovascular shock (Kilbourn, Traber, and Szabo). IFN-gamma is required for progression of chronic intestinal inflammation in such diseases as Crohn's disease and inflammatory bowel disease (IBD) presumably through the intermediacy of CD4+ lymphocytes probably of the TH1 phenotype (Sartor). An elevated level of serum IgE is associated with various atopic diseases such as bronchial asthma and atopic dermatitis. The level of IFN-gamma was negatively correlated with serum IgE suggesting a role for IFNgamma in atopic patients (Teramoto et al.).

The proinflammatory cytokine, IL-1-beta, is partially controlled by MAPKAP-k2. Hence, inhibition of MAPKAP-k2 may impact IL-1-beta dependent processes. IL-1 has been implicated as an immunological effector molecule in a large number of disease processes. IL-1 receptor antagonist (IL-1ra) had been examined in human clinical trials. Efficacy has been demonstrated for the treatment of rheumatoid arthritis (Antril, Amgen). In a phase III human clinical trial IL-1 ra reduced the mortality rate in patients with septic shock syndrome (Dinarello). Several other diseases affected by IL-1 include Adult Onset Still's disease, macrophage auto-activation syndromes, Muckle-Wells syndrome, Familial Cold Autoinflammatory Syndrome and Neonatal Onset Multisystem Inflammatory Disease (Dinarello). Patients with Muckle-Wells syndrome exhibiting systemic inflammation were treated with anakinra (IL-1ra), leukocytosis serum amyloid A, C-reactive protein and local inflammatory arthritis were reduced with a few days demonstrating that systemic inflammation is IL-1 mediated (Hawkins et al.).

Osteoarthritis is a slow progressive disease characterized by destruction of the articular cartilage. IL-1 is detected in synovial fluid and in the cartilage matrix of osteoarthritic joints. Antagonists of IL-1 have been shown to diminish the degradation of cartilage matrix components in a variety of experimental models of arthritis (Chevalier). Nitric oxide (NO) is a mediator of cardiovascular homeostasis, neurotransmission and immune function; recently it has been shown to have important effects in the modulation of bone remodeling. Cytokines such as IL-1 and TNF are potent stimulators of NO production. NO is an important regulatory molecule in bone with effects on cells of the osteoblast and osteoclast lineage (Evans and Ralston). The promotion of beta-cell destruction leading to insulin dependent diabetes mellitus shows dependence on IL-1. Some of this damage may be mediated through other effectors such as prostaglandins and thromboxanes. IL-1 can effect this process by controlling the level of both cyclooxygenase II and inducible nitric oxide synthetase expression (McDaniel et al.).

Inhibitors of cytokine production are expected to block inducible cyclooxygenase (COX-2) expression. COX-2 expression has been shown to be increased by cytokines and it is believed to be the isoform of cyclooxygenase responsible for inflammation (O'Banion, Winn, and Young). Accordingly, inhibitors of MAPKAP-k2 reducing the production of cytokines such as IL-1, would be expected to exhibit efficacy against those disorders currently treated with COX inhibitors such as the familiar NSAIDs. These disorders include acute and chronic pain as well as symptoms of inflammation and cardiovascular disease.

Elevation of several cytokines has been demonstrated during active inflammatory bowel disease (IBD). A mucosal imbalance of intestinal IL-1 and IL-1 ra is present in patients with IBD. Insufficient production of endogenous IL-1 ra may contribute to the pathogenesis of IBD (Cominelli and Pizarro). Alzheimer disease is characterized by the presence of beta-amyloid protein deposits, neurofibrillary tangles and cholinergic dysfunction throughout the hippocampal region. The structural and metabolic damage found in Alzheimer disease is possibly due to a sustained elevation of IL-1 (Holden and Mooney). A role for IL-1 in the pathogenesis of human immunodeficiency virus (HIV) has been identified. IL-1 ra showed a clear relationship to acute inflammatory events as well as to the different disease stages in the pathophysiology of HIV infection (Kreuzer et al.). IL-1 and TNF are both involved in periodontal disease. The destructive process associated with periodontal disease may be due to a disregulation of both IL-1 and TNF (Howells).

IL-1 has also been shown to induce uveitis in rats which could be inhibited with IL-1 blockers (Xuan et al.). Cytokines including IL-1, TNF and GM-CSF have been shown to stimulate proliferation of acute myelogenous leukemia blasts (Bruserud). IL-1 was shown to be essential for the development of both irritant and allergic contact dermatitis. Epicutaneous sensitization can be prevented by the administration of an anti-IL-1 monoclonal antibody before epicutaneous application of an allergen (Muller, Knop, and Enk). Data obtained from IL-1 knock out mice indicates the critical involvement in fever for this cytokine (Kluger et al.). A variety of cytokines including TNF, IL-1, IL-6 and IL-8 initiate the acute-phase reaction which is stereotyped in fever, malaise, myalgia, headaches, cellular hypermetabolism and multiple endocrine and enzyme responses (Beisel). The production of these inflammatory cytokines rapidly follows trauma or pathogenic organism invasion.

This patent discloses compounds that have the ability to inhibit TNF-alpha. Compounds disclosed herein are indicated to be effective in treating the following diseases: Rheumatoid arthritis, psoriasis, crohn's disease, dementia associated with HIV infection, glaucoma, optic-neuropathy, optic neuritis, retinal ischemia, laser induced optic damage, surgery or trauma-induced proliferative vitreoretinopathy, cerebral ischemia, hypoxia-ischemia, hypoglycemia, domoic acid poisoning, anoxia, carbon monoxide or manganese or cyanide poisoning, Huntington's disease, Alzheimer's disease, Parkinson's disease, meningitis, multiple sclerosis and other demyelinating diseases, amyotrophic lateral sclerosis, head and spinal cord trauma, seizures, convulsions, olivopontocerebellar atrophy, neuropathic pain syndromes, diabetic neuropathy, HIV-related neuropathy, MERRF and MELAS syndromes, Leber's disease, Wernicke's encephalopathy, Rett syndrome, homocysteinuria, hyperprolinemia, hyperhomocysteinemia, nonketotic hyperglycinemia, hydroxybutyric aminoaciduria, sulfite oxidase deficiency, combined systems disease, lead encephalopathy, Tourett's syndrome, hepatic encephalopathy, drug addiction, drug tolerance, drug dependency, depression, anxiety and schizophrenia. In addition, compounds dislosed herein are useful for treating acute and chronic inflammation in the lung caused by inhalation of smoke such as cigarette smoke. TNF-alpha anatagonists are apparently also useful for the treatment of endometriosis, see EP 1022027 A1. Infliximab® of rheumatoid arthritis, psoriasis, ankylosing spondylitis, and psoriatic arthritis. The p38MAP kinase pathway plays an role in B. burgdorferi-elicited infammation and may be useful in treating inflammation induced by the Lyme disease agent. Anguita, J. et. al., *The Journal of Immunology*, 2002, 168:6352-6357.

The work cited above supports the principle that inhibition of cytokine production will be beneficial in the treatment of cytokine mediated diseases. Therefore a need exists for small molecule inhibitors for treating these diseases with optimized efficacy, pharmacokinetic and safety profiles.

REFERENCE LIST

Abbott Laboratories receives FDA approval earlier than anticipated for HUMIRA (Adalimumab) for the treatment of rheumatoid arthritis (RA). *Company Press Release (Abbott Lab.)*, Dec. 31, 2002 (2002).

Ablamunits, V., et al. "Islet T cells secreting IFN-gamma in NOD mouse diabetes: arrest by p277 peptide treatment." *J Autoimmun.* 11.1 (1998): 73-81.

Akaike, T., M. Suga, and H. Maeda. "Free radicals in viral pathogenesis: molecular mechanisms involving superoxide and NO." *Proc. Soc. Exp Biol Med* 217.1 (1998): 64-73.

Alexander, J., et al. "Mechanisms of innate resistance to *Toxoplasma gondii* infection." *Philos. Trans. R. Soc. Lond B Biol Sci.* 352.1359 (1997): 1355-59.

Beisel, W. R. "Herman Award Lecture, 1995: infection-induced malnutrition—from cholera to cytokines." *Am J Clin Nutr.* 62.4 (1995): 813-19.

Bonay, M., et al. "Characterization of proliferative responses and cytokine mRNA profiles induced by Vespula venom in patients with severe reactions to wasp stings." *Clin Exp Immunol* 109.2 (1997): 342-50.

Borjesson, A., et al. "TNF-alpha stimulates alveolar liquid clearance during intestinal ischemia-reperfusion in rats." *Am J Physiol Lung Cell Mol Physiol* 278.1 (2000): L3-12.

Bruserud, O. "Effects of endogenous interleukin 1 on blast cells derived from acute myelogenous leukemia patients." *Leuk. Res* 20.1 (1996): 65-73.

bu-Amer, Y., et al. "Tumor necrosis factor receptors types 1 and 2 differentially regulate osteoclastogenesis." *J Biol. Chem.* 275.35 (2000): 27307-10.

Burke, G. W., et al. "Early development of acute myelogenous leukemia following kidney transplantation: possible role of multiple serum cytokines." *Leuk. Lymphoma* 19.1-2 (1995): 173-80.

Chevalier, X. "Upregulation of enzymatic activity by interleukin-1 in osteoarthritis." *Biomed. Pharmacother.* 51.2 (1997): 58-62.

Chisari, F. V. and C. Ferrari. "Hepatitis B virus immunopathology." *Springer Semin. Immunopathol.* 17.2-3 (1995): 261-81.

Cominelli, F. and T. T. Pizarro. "Interleukin-1 and interleukin-1 receptor antagonist in inflammatory bowel disease." *Aliment. Pharmacol Ther* 10 Suppl 2 (1996): 49-53.

Dinarello, C. A. "Interleukin-1 and interleukin-1 receptor antagonist." *Nutrition* 11.5 Suppl (1995): 492-94.
"Interleukin-1." *Rev. Infect. Dis.* 6.1 (1984): 51-95.
"Therapeutic strategies to reduce IL-1 activity in treating local and systemic inflammation." *Curr. Opin. Pharmacol.* 4.4 (2004): 378-85.

Elhage, R., et al. "Differential effects of interleukin-1 receptor antagonist and tumor necrosis factor binding protein on fatty-streak formation in apolipoprotein E-deficient mice." *Circulation* 97.3 (1998): 242-44.

Ershler, W. B., S. M. Harman, and E. T. Keller. "Immunologic aspects of osteoporosis." *Dev. Comp Immunol* 21.6 (1997): 487-99.

Evans, D. M. and S. H. Ralston. "Nitric oxide and bone." *J Bone Miner. Res* 11.3 (1996): 300-05.

Feldman, A. M., et al. "The role of tumor necrosis factor in the pathophysiology of heart failure." *J Am Coll. Cardiol.* 35.3 (2000): 537-44.

Geng, Y. J. "Regulation of programmed cell death or apoptosis in atherosclerosis." *Heart Vessels* Suppl 12 (1997): 76-80.

Gruol, D. L. and T. E. Nelson. "Physiological and pathological roles of interleukin-6 in the central nervous system." *Mol Neurobiol.* 15.3 (1997): 307-39.

Hawkins, P. N., et al. "Spectrum of clinical features in Muckle-Wells syndrome and response to anakinra." *Arthritis Rheum.* 50.2 (2004): 607-12.

Hayden, F. G., et al. "Local and systemic cytokine responses during experimental human influenza A virus infection. Relation to symptom formation and host defense." *J Clin Invest* 101.3 (1998): 643-49.

Higham, M. A., et al. "Tumour necrosis factor-alpha gene promoter polymorphism in chronic obstructive pulmonary disease." *Eur Respir J* 15.2 (2000): 281-84.

Holden, R. J. and P. A. Mooney. "Interleukin-1 beta: a common cause of Alzheimer's disease and diabetes mellitus." *Med Hypotheses* 45.6 (1995): 559-71.

Holden, R. J. and I. S. Pakula. "The role of tumor necrosis factor-alpha in the pathogenesis of anorexia and bulimia nervosa, cancer cachexia and obesity." *Med Hypotheses* 47.6 (1996): 423-38.

Howells, G. L. "Cytokine networks in destructive periodontal disease." *Oral Dis.* 1.4 (1995): 266-70.

Ihle, J. N. "The challenges of translating knockout phenotypes into gene function." *Cell* 102.2 (2000): 131-34.

Ito, H., et al. "A pilot randomized trial of a human anti-interleukin-6 receptor monoclonal antibody in active Crohn's disease." *Gastroenterology* 126.4 (2004): 989-96.

Jaffray, C., J. Yang, and J. Norman. "Elastase mimics pancreatitis-induced hepatic injury via inflammatory mediators." *J Surg. Res* 90.2 (2000): 95-101.

Jarvis, B. and D. Faulds. "Etanercept: a review of its use in rheumatoid arthritis." *Drugs* 57.6 (1999): 945-66.

Kilbourn, R. G., D. L. Traber, and C. Szabo. "Nitric oxide and shock." *Dis. Mon.* 43.5 (1997): 277-348.

Kluger, M. J., et al. "The use of knockout mice to understand the role of cytokines in fever." *Clin Exp Pharmacol Physiol* 25.2 (1998): 141-44.

Koch, A. E., S. L. Kunkel, and R. M. Strieter. "Cytokines in rheumatoid arthritis." *J. Investig. Med.* 43.1 (1995): 28-38.

Kotlyarov, A., et al. "MAPKAP kinase 2 is essential for LPS-induced TNF-alpha biosynthesis." *Nat. Cell Biol.* 1.2 (1999): 94-97.

Kotlyarov, A., et al. "Distinct cellular functions of MAPKAP-K2." *Mol. Cell Biol.* 22.13 (2002): 4827-35.

Kreuzer, K. A., et al. "The IL-1 system in HIV infection: peripheral concentrations of IL-1beta, IL-1 receptor antagonist and soluble IL-1 receptor type II." *Clin Exp Immunol* 109.1 (1997): 54-58.

Kyriakis, J. M. and J. Avruch. "Mammalian mitogen-activated protein kinase signal transduction pathways activated by stress and inflammation." *Physiol Rev.* 81.2 (2001): 807-69.

Lahdevirta, J., et al. "Elevated levels of circulating cachectin/tumor necrosis factor in patients with acquired immunodeficiency syndrome." *Am J Med* 85.3 (1988): 289-91.

Le, Hir M., et al. "Prevention of crescentic glomerulonephritis induced by anti-glomerular membrane antibody in tumor necrosis factor-deficient mice." *Lab Invest* 78.12 (1998): 1625-31.

Lemay, S., et al. "Prominent and sustained up-regulation of gp130-signaling cytokines and the chemokine MIP-2 in murine renal ischemia-reperfusion injury." *Transplantation* 69.5 (2000): 959-63.

Loffreda, S., et al. "Leptin regulates proinflammatory immune responses." *FASEB J* 12.1 (1998): 57-65.

Martino, G., et al. "Proinflammatory cytokines regulate antigen-independent T-cell activation by two separate calcium-signaling pathways in multiple sclerosis patients." *Ann. Neurol* 43.3 (1998): 340-49.

McDaniel, M. L., et al. "Cytokines and nitric oxide in islet inflammation and diabetes." *Proc. Soc. Exp Biol Med* 211.1 (1996): 24-32.

Mease, P. J., et al. "Etanercept in the treatment of psoriatic arthritis and psoriasis: a randomised trial." *Lancet* 356.9227 (2000): 385-90.

Melchiorri, C., et al. "Enhanced and coordinated in vivo expression of inflammatory cytokines and nitric oxide synthase by chondrocytes from patients with osteoarthritis." *Arthritis Rheum.* 41.12 (1998): 2165-74.

Mills, B. G. and A. Frausto. "Cytokines expressed in multinucleated cells: Paget's disease and giant cell tumors versus normal bone." *Calcif. Tissue Int* 61.1 (1997): 16-21.

Mitsui, Y., et al. "The expression of proinflammatory cytokine mRNA in the sciatic-tibial nerve of ischemia-reperfusion injury." *Brain Res* 844.1-2 (1999): 192-95.

Muller, G., J. Knop, and A. H. Enk. "Is cytokine expression responsible for differences between allergens and irritants?" *Am J Contact Dermat.* 7.3 (1996): 177-84.

Neininger, A., et al. "MAPKAP-K2 targets AU-rich elements and regulates biosynthesis of tumor necrosis factor and interleukin-6 independently at different post-transcriptional levels." *J. Biol. Chem.* 277.5 (2002): 3065-68.

Nishimoto, N. and T. Kishimoto. "Inhibition of IL-6 for the treatment of inflammatory diseases." *Curr. Opin. Pharmacol.* 4.4 (2004): 386-91.

Nuki, G., et al. "Long-term safety and maintenance of clinical improvement following treatment with anakinra (recombinant human interleukin-1 receptor antagonist) in patients with rheumatoid arthritis: extension phase of a randomized, double-blind, placebo-controlled trial." *Arthritis Rheum.* 46.11 (2002): 2838-46.

O'Banion, M. K., V. D. Winn, and D. A. Young. "cDNA cloning and functional activity of a glucocorticoid-regulated inflammatory cyclooxygenase." *Proc. Natl. Acad. Sci. U.S.A* 89.11 (1992): 4888-92.

Parkman, R. "Chronic graft-versus-host disease." *Curr. Opin. Hematol.* 5.1 (1998): 22-25.

Phillips, K., et al. "Arthritis suppressor genes TIA-1 and TTP dampen the expression of tumor necrosis factor alpha, cyclooxygenase 2, and inflammatory arthritis." *Proc. Natl. Acad. Sci. U.S.A* 101.7 (2004): 2011-16.

Present, D. H., et al. "Infliximab for the treatment of fistulas in patients with Crohn's disease." *N. Engl. J. Med.* 340.18 (1999): 1398-405.

Rankin, E. C., et al. "The therapeutic effects of an engineered human anti-tumour necrosis factor alpha antibody (CDP571) in rheumatoid arthritis." *Br. J. Rheumatol.* 34.4 (1995): 334-42.

Renzetti, L. M. and P. R. Gater. "Ro 45-2081, a TNF receptor fusion protein, prevents inflammatory responses in the airways." *Inflamm. Res.* 46 Suppl 2 (1997): S143-S144.

Rutgeerts, P. J. "Review article: efficacy of infliximab in Crohn's disease-induction and maintenance of remission." *Aliment. Pharmacol. Ther.* 13 Suppl 4 (1999): 9-15.

Sartor, R. B. "Cytokine regulation of experimental intestinal inflammation in genetically engineered and T-lymphocyte reconstituted rodents." *Aliment. Pharmacol Ther* 10 Suppl 2 (1996): 36-42.

Scholz, D., et al. "Inhibition of Fc epsilon RI-mediated activation of mast cells by 2,3,4-trihydropyrimidino[2,1-a]isoquinolines." *J Med. Chem.* 41.7 (1998): 1050-59.

Shohami, E., et al. "Cytokine production in the brain following closed head injury: dexanabinol (HU-211) is a novel TNF-alpha inhibitor and an effective neuroprotectant." *J Neuroimmunol.* 72.2 (1997): 169-77.

Simpson, R. J., et al. "Interleukin-6: structure-function relationships." *Protein Sci.* 6.5 (1997): 929-55.

Stack, W. A., et al. "Randomised controlled trial of CDP571 antibody to tumour necrosis factor-alpha in Crohn's disease." *Lancet* 349.9051 (1997): 521-24.

Strassmann, G. and T. Kambayashi. "Inhibition of experimental cancer cachexia by anti-cytokine and anti-cytokine-receptor therapy." *Cytokines Mol Ther* 1.2 (1995): 107-13.

Szepietowski, J. C., et al. "Atopic and non-atopic individuals react to nickel challenge in a similar way. A study of the cytokine profile in nickel-induced contact dermatitis." *Br J Dermatol.* 137.2 (1997): 195-200.

Takabatake, N., et al. "The relationship between chronic hypoxemia and activation of the tumor necrosis factor-alpha system in patients with chronic obstructive pulmonary disease." *Am J Respir Crit Care Med* 161.4 Pt 1 (2000): 1179-84.

Tamura, K., et al. "Requirement for p38alpha in erythropoietin expression: a role for stress kinases in erythropoiesis." *Cell* 102.2 (2000): 221-31.

Tashiro, H., et al. "Role of cytokines in the pathogenesis of restenosis after percutaneous transluminal coronary angioplasty." *Coron. Artery Dis.* 12.2 (2001): 107-13.

Taylor, G. A., et al. "A pathogenetic role for TNF alpha in the syndrome of cachexia, arthritis, and autoimmunity resulting from tristetraprolin (TTP) deficiency." *Immunity.* 4.5 (1996): 445-54.

Teramoto, T., et al. "Serum IgE level is negatively correlated with the ability of peripheral mononuclear cells to produce interferon gamma (IFNgamma): evidence of reduced expression of IFNgamma mRNA in atopic patients." *Clin Exp Allergy* 28.1 (1998): 74-82.

Terregino, C. A., et al. "Endogenous mediators in emergency department patients with presumed sepsis: are levels associated with progression to severe sepsis and death?" *Ann. Emerg. Med* 35.1 (2000): 26-34.

Tibbles, L. A. and J. R. Woodgett. "The stress-activated protein kinase pathways." *Cell. Mol. Life Sci.* 55.10 (1999): 1230-54.

Treon, S. P. and K. C. Anderson. "Interleukin-6 in multiple myeloma and related plasma cell dyscrasias." *Curr. Opin. Hematol.* 5.1 (1998): 42-48.

Udomsangpetch, R., et al. "Involvement of cytokines in the histopathology of cerebral malaria." *Am J Trop. Med Hyg.* 57.5 (1997): 501-06.

Weinblatt, M. E., et al. "A trial of etanercept, a recombinant tumor necrosis factor receptor:Fc fusion protein, in patients with rheumatoid arthritis receiving methotrexate." *N. Engl. J. Med.* 340.4 (1999): 253-59.

"Anti-tumor necrosis factor ameliorates joint disease in murine collagen-induced arthritis." *Proc. Natl. Acad. Sci. U.S.A* 89.20 (1992): 9784-88.

Xuan, B., et al. "Effective treatment of experimental uveitis with interleukin-1 blockers, CK 123 and CK 124." *J Ocul. Pharmacol Ther* 14.1 (1998): 31-44.

BRIEF SUMMARY OF THE INVENTION

The work cited above supports the principle that inhibition of MAPKAP-k2 will be beneficial in the treatment of various disease states.

It is therefore an object of the invention to provide amide compounds of formulas I and IA:

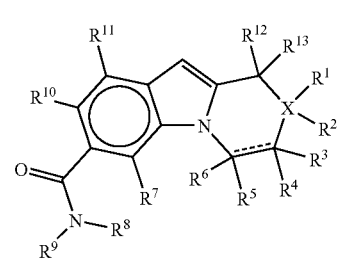

I

-continued

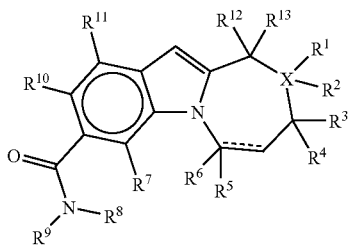

wherein X and $R^1$-$R^{13}$ of formulas (I) and (IA) are defined below, which inhibit the activity of MAPKAP-k2.

It is a further object of the invention to provide methods for treating MAPKAP-k2 mediated diseases and pathological conditions involving inflammation such as chronic inflammatory disease, using the novel compounds of the invention.

It is yet a further object of the invention to provide processes of preparation of the above-mentioned novel compounds.

DETAILED SUMMARY OF THE INVENTION

In an embodiment of the present invention, there is provided a compound, salt, isomer, or product thereof, that is effective for treating or preventing a disease or disorder in a subject, which diseases or disorders can be treated or prevented by inhibiting the activity of MAPKAP-k2, wherein the compound has the structure:

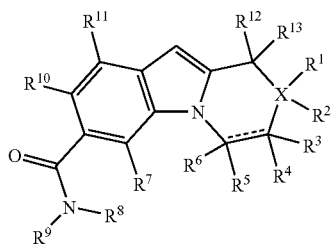

wherein:

X is C or N $R^1$ is hydrogen, hydroxy, carbamoyl, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{3-7}$ cycloalkyl, or $C_{1-6}$alkylthio $C_{1-6}$alkyl, wherein the sulfur atom, when present, is optionally oxidized to a sulfoxide or sulfone;

$R^2$ is optionally present and, if present, is hydrogen, hydroxy, ureido, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{3-7}$ cycloalkyl, or $C_{1-6}$ alkylthio, wherein the sulfur atom, when present, is optionally oxidized to a sulfoxide or sulfone;

$R^3$ is hydrogen, amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{1-6}$ alkynyl, $C_{1-6}$ alkoxy, $C_{2-6}$ alkenyloxy, $C_{2-6}$ alkynyloxy, hydroxy, $C_{3-7}$ cycloalkyl, carbamoyl, $CO_2C_{1-6}$alkyl, or $C_{1-6}$ alkylthio wherein the sulfur atom is optionally oxidized to a sulfoxide or sulfone; wherein each alkyl, amino, cycloalkyl, alkenyl, alkoxy, alkenyloxy, alkynyloxy, carbonyl, carbamoyl, and alkylthio group is optionally substituted by $R^x$ wherein $R^x$ can be chosen from:

hydrogen, amino, $C_{1-6}$alkyl, $C_{2-6}$ alkenyl, amino $C_{1-6}$ alkyl, hydroxy$C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, carbonyl, carbamoyl, ureido, -$CO_2C_{1-6}$alkyl or $C_{2-6}$ alkylthio wherein the sulfur atom is oxidized to a sulfoxide or sulfone;

$R^4$ is optionally present and, when present, is hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{1-6}$ alkynyl, $C_{1-6}$ alkoxy, $C_{2-6}$ alkenyloxy, $C_{2-6}$ alkynyloxy, hydroxy, $C_{3-7}$ cycloalkyl, carbonyl, carbamoyl, or $C_{1-6}$ alkylthio wherein the sulfur atom is optionally oxidized to a sulfoxide or sulfone; wherein each alkyl, amino, cycloalkyl, alkenyl, alkoxy, alkenyloxy, alkynyloxy, carbonyl, carbamoyl, and alkylthio group is optionally substituted by $R^x$, and wherein $R^x$ can be chosen from:

amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-16}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, carbonyl, carbamoyl, ureido, or $C_{2-6}$ alkylthio wherein the sulfur atom is oxidized to a sulfoxide or sulfone;

$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$ alkyl, di$C_{1-6}$alkylamino$C_{1-6}$alkyl, hydroxy, $C_{3-7}$ cycloalkyl, heterocyclyl, heterocyclyl$C_{1-6}$alkyl, aryl, aryloxy, acyl, heteroaryl, or $C_{1-6}$ alkylthio, wherein the sulfur atom is oxidized to a sulfoxide or sulfone, and wherein each alkyl, cycloalkyl, alkenyl, aryl is optionally substituted by $R^x$, which is defined hereinabove, or =N—OH, =N—NHheteroaryl;

$R^4$ and $R^5$, along with their substituents, may optionally be taken together to form a $C_{3-8}$ cycloalkyl optionally substituted with amino, $C_{1-3}$ alkyl, halogen, or hydroxy;

$R^6$ is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, or $C_{1-6}$ alkylthio, wherein the sulfur atom is oxidized to a sulfoxide or sulfone, and wherein each alkyl, cycloalkyl, alkenyl, aryl is optionally substituted with single or multiple $R^x$, which is defined hereinabove, or $R^5$ and $R^6$, along with their substituents, may optionally be taken together to form a $C_{3-7}$ cycloalkyl that may be optionally substituted with single or multiple $R^x$, which is defined hereinabove;

$R^7$ is selected from hydrogen, $C_{1-6}$ alkyl, $C_{3-7}$ cycloalkyl, $C_{1-6}$ alkoxy, C1-6alkoxyC1-6 alkyl, hydroxy, hydroxy $C_{1-6}$ alkyl or amino optionally mono- or di-substituted by $C_{1-6}$ alkyl, aryl or aryl C1-6 alkyl, or $R^7$ may be halo, haloalkyl, alkoxy, carboxyl, carbamoyl, nitro, dialkylamino, benzyloxy, hydrazinocarbonyl, alkoxycarbonyl, alkoxycarbonylheterocyclcarbonyl, or hydroxy;

wherein each alkyl, cycloalkyl, alkenyl, aryl or heteroaryl is optionally substituted with single or multiple $R^x$, which is defined hereinabove, $R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;

$R^9$ is chosen from hydrogen, halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-16}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl or $C_{2-6}$ alkylthio, wherein the sulfur atom is optionally oxidized to a sulfoxide or sulfone; wherein each aryl, heterocycle or heteroaryl may be singly or multiply substituted with $R^y$, wherein $R^y$ may be chosen from:

halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl optionally substituted with $R^x$, aryloxy, acyl, heteroaryl optionally substituted with $R^x$, $C_{3-7}$ cycloalkyl-$C_{1-6}$ alkyl, aryl-$C_{1-6}$ alkyl, aryl-$C_{1-6}$ haloalkyl, aryl-$C_{1-6}$aminoalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, $C_{2-6}$ alkylthio wherein the sulfur atom is optionally oxidized to a sulfoxide or sulfone, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$, —$C(O)N(R^a)(R^b)$ where $R^a$ and $R^b$ are independently selected from H, $C_{1-3}$alkyl, —$CH_2C(O)NH_2$, —$(CH_2)_nOH$, —$(CH_2)_nNR^cR^d$, where n=2 or 3 and $R^c$ and $R^d$ are independently selected from H, $C_{1-3}$alkyl and $C(O)CH_3$, or —C(O)NH—N=C—$R^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —$CO_2C_{1-3}$alkyl, —$C(O)NH_2$, —OH, $C_{1-3}$alkyl, amino, $C_{1-3}$alkylamino and di$C_{1-3}$alkylamino; or $R^8$ and $R^9$ can be taken together to form a cycloalkyl or heteraryl ring;

$R^{10}$ and $R^{11}$ are independently selected from hydrogen, $C_{1-6}$ alkoxy, hydroxy, halo, $C_{1-6}$ alkyl, $C_{3-7}$ cycloalkyl;

$R^{12}$ is selected from =S, oxo, $C_{1-6}$ alkyl, cyano, aminoalkyl, amino, haloalkyl, hydroxyalkyl, =N—$OR^z$, =N—$N(R^z)_2$, wherein $R^z$ is selected from hydrogen or $C_{1-6}$ alkyl, $R^{13}$ is optionally present and, if present, is selected from hydrogen, $C_{1-6}$ alkyl, or a halo group.

In a second embodiment there are provided compounds of formula (I) as described above and wherein X is C or N;

$R^1$ is hydrogen;

$R^2$ is optionally present and, if present, is hydrogen;

$R^3$ is hydrogen, $C_{1-6}$ alkyl, amino $C_{1-6}$ alkyl, hydroxy$C_{1-6}$ alkyl, cyano $C_{1-6}$ alkyl, $C_{3-7}$ cycloalkyl, carbamoyl or $CO_2C_{1-6}$alkyl; wherein each alkyl, amino, cycloalkyl or carbamoyl group is optionally substituted by $R^x$ wherein $R^x$ can be chosen from:

hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbonyl, carbamoyl, or —$CO_2C_{1-6}$alkyl;

$R^4$ is optionally present and, when present, is hydrogen or $C_{1-6}$alkyl;

$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$alkyl, di$C_{1-6}$alkylamino$C_{1-6}$alkyl, hydroxy, heterocyclyl$C_{1-6}$alkyl, wherein the heterocyclyl is chosen from pyrrolidinyl, piperidinyl, piperazinyl, and morpholinyl, $C_{3-7}$ cycloalkyl, acyl, =N—OH or =N—NHheteroaryl;

$R^6$ is hydrogen or $C_{1-6}$ alkyl, optionally partially or fully halogenated, or $R^5$ and $R^6$, may optionally be taken together to form a $C_{3-7}$ cycloalkyl;

$R^7$ is hydrogen, hydroxyl or $C_{1-6}$ alkoxy;

$R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;

$R^9$ is chosen from hydrogen, $C_{1-6}$ alkyl, piperidinyl, phenyl and heteroaryl, wherein each phenyl, piperidinyl or heteroaryl may be singly or multiply substituted with $R^y$, wherein $R^y$ may be chosen from:

halogen, $C_{1-6}$ alkyl, $C_{2-6}$ alkenyl, $C_{1-6}$ alkoxy, hydroxy, $C_{3-7}$ cycloalkyl, phenyl, phenoxy, acyl, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$, —$C(O)N(R^a)(R^b)$ where $R^a$ and $R^b$ are independently selected from H, $C_{1-3}$alkyl, —$CH_2C(O)NH_2$, —$(CH_2)_nOH$ and —$(CH_2)_nNR^cR^d$, where n=2 or 3 and $R^c$ and $R^d$ are independently selected from H, $C_{1-3}$alkyl and $C(O)CH_3$, or —C(O)NH—N=C—$R^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —$CO_2C_{1-3}$alkyl, —$C(O)NH_2$, —OH, $C_{1-3}$alkyl, amino, $C_{1-3}$alkylamino and di$C_{1-3}$ alkylamino;

$R^{10}$ and $R^{11}$ are hydrogen;

$R^{12}$ is selected from =S, oxo, $C_{1-6}$ alkyl, cyano, aminoalkyl, amino, haloalkyl, hydroxyalkyl, =N—$OR^z$, =N—$N(R^z)_2$, wherein $R^z$ is selected from hydrogen or $C_{1-6}$ alkyl; and $R^{13}$ is optionally present and, if present, is selected from from hydrogen, $C_{1-6}$ alkyl, or a halo group.

In another embodiment there are provided compounds of formula (I) as described above and wherein X is C or N;

$R^1$ is hydrogen;

$R^2$ is optionally present and, if present, is hydrogen;

$R^3$ is hydrogen, $C_{1-6}$ alkyl, amino $C_{1-6}$ alkyl, hydroxy$C_{1-6}$ alkyl, cyano $C_{1-6}$ alkyl, $C_{3-7}$ cycloalkyl, carbamoyl or $CO_2C_{1-6}$alkyl; wherein each alkyl, amino, cycloalkyl or carbamoyl group is optionally substituted by $R^x$ wherein $R^x$ can be chosen from:

hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbonyl, carbamoyl, or —$CO_2C_{1-6}$alkyl;

$R^4$ is optionally present and, when present, is hydrogen or $C_{1-6}$alkyl;

$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$alkyl, di$C_{1-6}$alkylamino$C_{1-6}$alkyl, hydroxy, heterocyclyl$C_{1-6}$alkyl, wherein the heterocyclyl is chosen from pyrrolidinyl, piperidinyl, piperazinyl, and morpholinyl, $C_{3-7}$ cycloalkyl, acyl, =N—OH or =N—NHheteroaryl;

$R^6$ is hydrogen or $C_{1-6}$ alkyl, optionally partially or fully halogenated, or $R^5$ and $R^6$, may optionally be taken together to form a $C_{3-7}$ cycloalkyl;

$R^7$ is hydrogen, hydroxyl or $C_{1-6}$ alkoxy;

$R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;

$R^9$ is chosen from hydrogen, $C_{1-6}$ alkyl, piperidinyl, phenyl, heteroaryl selected from pyridyl, quinolinyl, thiazolyl, indolyl, benzothiazolyl, benzoxazolyl, isoxazolyl, pyrazinyl, pyrimidinyl, benzimidazolyl, oxazolyl, pyrazolyl, 1,3,4-thiadiazolyl, tetrazolyl, 1,3,4-oxadiazolyl, 1,2,4-triazolyl, imidazolyl, pyrrolyl, thiophene, benzothiophene, furanyl and benzofuran wherein each phenyl, piperidinyl or heteroaryl may be singly or multiply substituted with $R^y$, wherein $R^y$ may be chosen from:

halogen, $C_{1-6}$ alkyl, $C_{2-6}$ alkenyl, $C_{1-6}$ alkoxy, hydroxy, $C_{3-7}$ cycloalkyl, phenyl, phenoxy, acyl, —OCF$_3$, amino, $C_{1-3}$alkylamino, di$C_{1-3}$alkylamino, acylamino, hydroxyethylamino, —CN, —CO$_2$C$_{1-3}$alkyl, —CH$_2$NH$_2$, —C(O)N(R$^a$)(R$^b$) where R$^a$ and R$^b$ are independently selected from H, $C_{1-3}$alkyl, —CH$_2$C(O)NH$_2$, —(CH$_2$)$_n$OH and —(CH$_2$)$_n$NR$^c$R$^d$, where n=2 or 3 and R$^c$ and R$^d$ are independently selected from H, $C_{1-3}$alkyl and C(O)CH$_3$, or, —C(O)NH—N=C—R$^e$, where R$^e$ is aryl or heteroaryl optionally substituted with R$^x$, or R$^a$ and R$^b$ together with the N they are connected to can form a pyrrolidine, piperazine, piperidine or morpholine ring optionally substituted with one to three groups selected from —CO$_2$C$_{1-3}$alkyl, —C(O)NH$_2$, —OH, $C_{1-3}$alkyl, amino, $C_{1-3}$alkylamino and di$C_{1-3}$alkylamino;

$R^{10}$ and $R^{11}$ are hydrogen;

$R^{12}$ is selected from =S, oxo, $C_{1-6}$ alkyl, cyano, aminoalkyl, amino, haloalkyl, hydroxyalkyl, =N—OR$^z$, =N—N(R$^z$)$_2$, wherein R$^z$ is selected from hydrogen or $C_{1-6}$ alkyl; and $R^{13}$ is optionally present and, if present, is selected from from hydrogen, $C_{1-6}$ alkyl, or a halo group.

In yet another embodiment there are provided compounds of formula (I) as described above and wherein X is N;

$R^1$ is hydrogen;

$R^3$ is hydrogen, $C_{1-6}$ alkyl, amino $C_{1-6}$ alkyl, hydroxy$C_{1-6}$ alkyl, cyano $C_{1-6}$ alkyl, $C_{3-7}$ cycloalkyl, carbamoyl or CO$_2$C$_{1-6}$alkyl; wherein each alkyl, amino, cycloalkyl or carbamoyl group is optionally substituted by R$^x$ wherein R$^x$ can be chosen from:

hydrogen, amino, $C_{1-6}$alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbonyl, carbamoyl, or —CO$_2$C$_{1-6}$alkyl;

$R^4$ is optionally present and, when present, is selected from hydrogen, or $C_{1-6}$alkyl;

$R^5$ is optionally present and, when present, is hydrogen, $C_{1-6}$ alkyl or CF$_3$;

$R^6$ is hydrogen, $C_{1-6}$ alkyl or CF$_3$; or $R^5$ and $R^6$, may optionally be taken together to form a $C_{3-7}$ cycloalkyl;

$R^7$ is hydrogen;

$R^8$ is hydrogen;

$R^9$ is chosen from hydrogen, $C_{1-6}$ alkyl, piperidinyl, phenyl, heteroaryl selected from pyridyl, quinolinyl, thiazolyl, indolyl, benzothiazolyl, benzoxazolyl, isoxazolyl, pyrazinyl, pyrimidinyl, benzimidazolyl, oxazolyl, pyrazolyl, 1,3,4-thiadiazolyl, tetrazolyl, 1,3,4-oxadiazolyl, 1,2,4-triazolyl, imidazolyl, pyrrolyl, thiophene, benzothiophene, furanyl and benzofuran, wherein each phenyl, piperidinyl or heteroaryl may be singly or multiply substituted with R$^y$, wherein R$^y$ may be chosen from:

halogen, $C_{1-6}$ alkyl, $C_{2-6}$ alkenyl, $C_{1-6}$ alkoxy, hydroxy, $C_{3-7}$ cycloalkyl, phenyl, phenoxy, acyl, —OCF$_3$, amino, $C_{1-3}$alkylamino, di$C_{1-3}$alkylamino, acylamino, hydroxyethylamino, —CN, —CO$_2$C$_{1-3}$alkyl, —CH$_2$NH$_2$ or —C(O)N(R$^a$)(R$^b$) where R$^a$ and R$^b$ are independently selected from H, $C_{1-3}$alkyl, —CH$_2$C(O)NH$_2$, —(CH$_2$)$_n$OH and —(CH$_2$)$_n$NR$^c$R$^d$, where n=2 or 3 and R$^c$ and R$^d$ are independently selected from H, $C_{1-3}$alkyl and C(O)CH$_3$, and —C(O)NH—N=C—R$^e$, where R$^e$ is phenyl, or R$^a$ and R$^b$ together with the N they are connected to can form a pyrrolidine, piperazine, piperidine or morpholine ring optionally substituted with one to three groups selected from —CO$_2$C$_{1-3}$alkyl, —C(O)NH$_2$, —OH, $C_{1-3}$alkyl, amino, $C_{1-3}$alkylamino and di$C_{1-3}$alkylamino;

$R^{10}$ and $R^{11}$ are hydrogen; and $R^{12}$ is oxo.

In a further embodiment of the invention these are provided compounds of the formula Ia:

wherein:

X is C or N $R^1$ is hydrogen, hydroxy, carbamoyl, $C_{1-6}$ alkyl, C2-6 alkenyl, C2-6 alkynyl, $C_{1-6}$ alkoxy, $C_{2-6}$ alkenyloxy, $C_{2-6}$ alkynyloxy, $C_{3-7}$ cycloalkyl, or $C_{1-6}$alkylthio $C_{1-6}$alkyl, wherein the sulfur atom, when present, is optionally oxidized to a sulfoxide or sulfone;

$R^2$ is optionally present and, if present, is hydrogen, hydroxy, ureido, $C_{1-6}$ alkyl, C2-6 alkenyl, C2-6 alkynyl, $C_{1-6}$ alkoxy, $C_{2-6}$ alkenyloxy, $C_{2-6}$ alkynyloxy, $C_{3-7}$ cycloalkyl, or $C_{1-6}$ alkylthio, wherein the sulfur atom, when present, is optionally oxidized to a sulfoxide or sulfone;

$R^3$ is hydrogen, amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{1-6}$ alkynyl, $C_{1-6}$ alkoxy, $C_{2-6}$ alkenyloxy, $C_{2-6}$ alkynyloxy, hydroxy, $C_{3-7}$ cycloalkyl, carbamoyl, $CO_2C_{1-6}$alkyl, or $C_{1-6}$ alkylthio wherein the sulfur atom is optionally oxidized to a sulfoxide or sulfone; wherein each alkyl, amino, cycloalkyl, alkenyl, alkoxy, alkenyloxy, alkynyloxy, carbonyl, carbamoyl, and alkylthio group is optionally substituted by $R^x$ wherein $R^x$ can be chosen from:
  hydrogen, amino, $C_{1-6}$alkyl, $C_{2-6}$ alkenyl, amino $C_{1-6}$ alkyl, hydroxy$C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, carbonyl, carbamoyl, ureido, —$CO_2C_{1-6}$alkyl or $C_{2-6}$ alkylthio wherein the sulfur atom is oxidized to a sulfoxide or sulfone;
$R^4$ is optionally present and, when present, is hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{1-6}$ alkynyl, $C_{1-6}$ alkoxy, $C_{2-6}$ alkenyloxy, $C_{2-6}$ alkynyloxy, hydroxy, $C_{3-7}$ cycloalkyl, carbonyl, carbamoyl, or $C_{1-6}$ alkylthio wherein the sulfur atom is optionally oxidized to a sulfoxide or sulfone; wherein each alkyl, amino, cycloalkyl, alkenyl, alkoxy, alkenyloxy, alkynyloxy, carbonyl, carbamoyl, and alkylthio group is optionally substituted by $R^x$, and wherein $R^x$ can be chosen from:
  amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-16}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, carbonyl, carbamoyl, ureido, or $C_{2-6}$ alkylthio wherein the sulfur atom is oxidized to a sulfoxide or sulfone;
$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$ alkyl, di$C_{1-6}$alkylamino$C_{1-6}$alkyl, hydroxy, $C_{3-7}$ cycloalkyl, heterocyclyl, heterocyclyl$C_{1-6}$alkyl, aryl, aryloxy, acyl, heteroaryl, or $C_{1-6}$ alkylthio, wherein the sulfur atom is oxidized to a sulfoxide or sulfone, and wherein each alkyl, cycloalkyl, alkenyl, aryl is optionally substituted by $R^x$, which is defined hereinabove, or =N—OH, =N—NHheteroaryl;
$R^4$ and $R^5$, along with their substituents, may optionally be taken together to form a $C_{3-8}$ cycloalkyl optionally substituted with amino, $C_{1-3}$ alkyl, halogen, or hydroxy;
$R^6$ is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, or $C_{1-6}$ alkylthio, wherein the sulfur atom is oxidized to a sulfoxide or sulfone, and wherein each alkyl, cycloalkyl, alkenyl, aryl is optionally substituted with single or multiple $R^x$, which is defined hereinabove, or
$R^5$ and $R^6$, along with their substituents, may optionally be taken together to form a $C_{3-7}$ cycloalkyl that may be optionally substituted with single or multiple $R^x$, which is defined hereinabove;

$R^7$ is selected from hydrogen, $C_{1-6}$ alkyl, $C_{3-7}$ cycloalkyl, $C_{1-6}$ alkoxy, C1-6alkoxyC1-6 alkyl, hydroxy, hydroxy $C_{1-6}$ alkyl or amino optionally mono- or di-substituted by $C_{1-6}$ alkyl, aryl or aryl C1-6 alkyl, or $R^7$ may be halo, haloalkyl, alkoxy, carboxyl, carbamoyl, nitro, dialkylamino, benzyloxy, hydrazinocarbonyl, alkoxycarbonyl, alkoxycarbonylheterocyclcarbonyl, or hydroxy; wherein each alkyl, cycloalkyl, alkenyl, aryl or heteroaryl is optionally substituted with single or multiple $R^x$, which is defined hereinabove,
$R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;
$R^9$ is chosen from hydrogen, halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-16}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl or $C_{2-6}$ alkylthio, wherein the sulfur atom is optionally oxidized to a sulfoxide or sulfone; wherein each aryl, heterocycle or heteroaryl may be singly or multiply substituted with $R^y$, wherein $R^y$ may be chosen from:
  halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl optionally substituted with $R^x$, aryloxy, acyl, heteroaryl optionally substituted with $R^x$, $C_{3-7}$ cycloalkyl-$C_{1-6}$ alkyl, aryl-$C_{1-16}$ alkyl, aryl-$C_{1-6}$ haloalkyl, aryl-$C_{1-6}$aminoalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, $C_{2-6}$ alkylthio wherein the sulfur atom is optionally oxidized to a sulfoxide or sulfone, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$, —C(O)N($R^a$)($R^b$) where $R^a$ and $R^b$ are independently selected from H, $C_{1-3}$alkyl, —$CH_2C(O)NH_2$, —$(CH_2)_nOH$, —$(CH_2)_nNR^cR^d$, where n=2 or 3 and $R^c$ and $R^d$ are independently selected from H, $C_{1-3}$alkyl and $C(O)CH_3$, or —C(O)NH—N=C—$R^e$, where $R^e$ is aryl or heteroaryl optionally substituted with $R^x$, or
  $R^a$ and $R^b$ together with the N they are connected to can form a pyrrolidine, piperazine, piperidine or morpholine ring optionally substituted with one to three groups selected from —$CO_2C_{1-3}$alkyl, —$C(O)NH_2$, —OH, $C_{1-3}$alkyl, amino, $C_{1-3}$alkylamino and di$C_{1-3}$ alkylamino; or
$R^8$ and $R^9$ can be taken together to form a cycloalkyl or heteraryl ring, with the proviso that it can not be morpholine;
$R^{10}$ and $R^{11}$ are independently selected from hydrogen, $C_{1-6}$ alkoxy, hydroxy, halo, $C_{1-6}$ alkyl, $C_{3-7}$ cycloalkyl;
$R^{12}$ is selected from =S, oxo, $C_{1-6}$ alkyl, cyano, aminoalkyl, amino, haloalkyl, hydroxyalkyl, =N—$OR^z$, =N—$N(R^z)_2$, wherein $R^z$ is selected from hydrogen or $C_{1-6}$ alkyl,
$R^{13}$ is optionally present and, if present, is selected from from hydrogen, $C_{1-6}$ alkyl, or a halo group.
In a second embodiment there are provided compounds of formula (I) as described above and wherein
X is C or N;
$R^1$ is hydrogen;
$R^2$ is optionally present and, if present, is hydrogen;

$R^3$ is hydrogen, $C_{1-6}$ alkyl, amino $C_{1-6}$ alkyl, hydroxy$C_{1-6}$ alkyl, cyano $C_{1-6}$ alkyl, $C_{3-7}$ cycloalkyl, carbamoyl or $CO_2C_{1-6}$alkyl; wherein each alkyl, amino, cycloalkyl or carbamoyl group is optionally substituted by $R^x$ wherein $R^x$ can be chosen from:

hydrogen, amino, $C_{1-6}$alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbonyl, carbamoyl, or —$CO_2C_{1-6}$alkyl;

$R^4$ is optionally present and, when present, is hydrogen or $C_{1-6}$alkyl;

$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$ alkyl, di$C_{1-6}$alkylamino$C_{1-6}$alkyl, hydroxy, heterocyclyl$C_{1-6}$alkyl, wherein the heterocyclyl is chosen from pyrrolidinyl, piperidinyl, piperazinyl, and morpholinyl, $C_{3-7}$ cycloalkyl, acyl, =N—OH or =N—NHheteroaryl;

$R^6$ is hydrogen or $C_{1-6}$ alkyl, optionally partially or fully halogenated, or $R^5$ and $R^6$, may optionally be taken together to form a $C_{3-7}$ cycloalkyl;

$R^7$ is hydrogen or $C_{1-6}$ alkoxy;

$R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;

$R^9$ is chosen from hydrogen, $C_{1-6}$alkyl, piperidinyl, phenyl and heteroaryl, wherein each phenyl, piperidinyl or heteroaryl may be singly or multiply substituted with $R^y$, wherein $R^y$ may be chosen from:

halogen, $C_{1-6}$ alkyl, $C_{2-6}$ alkenyl, $C_{1-6}$ alkoxy, hydroxy, $C_{3-7}$ cycloalkyl, phenyl, phenoxy, acyl, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$, —$C(O)N(R^a)(R^b)$ where $R^a$ and $R^b$ are independently selected from H, $C_{1-3}$alkyl, —$CH_2C(O)NH_2$, —$(CH_2)_nOH$ and —$(CH_2)_nNR^cR^d$, where n=2 or 3 and $R^c$ and $R^d$ are independently selected from H, $C_{1-3}$alkyl and $C(O)CH_3$, or —$C(O)NH$—N=C—$R^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —$CO_2C_{1-3}$alkyl, —$C(O)NH_2$, —OH, $C_{1-3}$alkyl, amino, $C_{1-3}$alkylamino and di$C_{1-3}$alkylamino;

$R^{10}$ and $R^{11}$ are hydrogen;

$R^{12}$ is selected from =S, oxo, $C_{1-6}$ alkyl, cyano, aminoalkyl, amino, haloalkyl, hydroxyalkyl, =N—$OR^z$, =N—$N(R^z)_2$, wherein $R^z$ is selected from hydrogen or $C_{1-6}$ alkyl; and $R^{13}$ is optionally present and, if present, is selected from from hydrogen, $C_{1-6}$ alkyl, or a halo group.

In another embodiment there are provided compounds of formula (I) as described above and wherein X is C or N;

$R^1$ is hydrogen;

$R^2$ is optionally present and, if present, is hydrogen;

$R^3$ is hydrogen, $C_{1-6}$ alkyl, amino $C_{1-6}$ alkyl, hydroxy$C_{1-6}$ alkyl, cyano $C_{1-6}$ alkyl, $C_{3-7}$ cycloalkyl, carbamoyl or $CO_2C_{1-6}$alkyl; wherein each alkyl, amino, cycloalkyl or carbamoyl group is optionally substituted by $R^x$ wherein $R^x$ can be chosen from:

hydrogen, amino, $C_{1-6}$alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbonyl, carbamoyl, or —$CO_2C_{1-6}$alkyl;

$R^4$ is optionally present and, when present, is hydrogen or $C_{1-6}$alkyl;

$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$ alkyl, di$C_{1-6}$alkylamino$C_{1-6}$alkyl, hydroxy, heterocyclyl$C_{1-6}$alkyl, wherein the heterocyclyl is chosen from pyrrolidinyl, piperidinyl, piperazinyl, and morpholinyl, $C_{3-7}$ cycloalkyl, acyl, =N—OH or =N—NHheteroaryl;

$R^6$ is hydrogen or $C_{1-6}$ alkyl, optionally partially or fully halogenated, or $R^5$ and $R^6$, may optionally be taken together to form a $C_{3-7}$ cycloalkyl;

$R^7$ is hydrogen, hydroxyl, or $C_{1-6}$ alkoxy;

$R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;

$R^9$ is chosen from hydrogen, $C_{1-6}$ alkyl, piperidinyl, phenyl, heteroaryl selected from pyridyl, quinolinyl, thiazolyl, indolyl, benzothiazolyl, benzoxazolyl, isoxazolyl, pyrazinyl, pyrimidinyl, benzimidazolyl, oxazolyl, pyrazolyl, 1,3,4-thiadiazolyl, tetrazolyl, 1,3,4-oxadiazolyl, 1,2,4-triazolyl, imidazolyl, pyrrolyl, thiophene, benzothiophene, furanyl and benzofuran wherein each phenyl, piperidinyl or heteroaryl may be singly or multiply substituted with $R^y$, wherein $R^y$ may be chosen from:

halogen, $C_{1-6}$ alkyl, $C_{2-6}$ alkenyl, $C_{1-6}$ alkoxy, hydroxy, $C_{3-7}$ cycloalkyl, phenyl, phenoxy, acyl, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$, —$C(O)N(R^a)(R^b)$ where $R^a$ and $R^b$ are independently selected from H, $C_{1-3}$alkyl, —$CH_2C(O)NH_2$, —$(CH_2)_nOH$ and —$(CH_2)_nNR^cR^d$, where n=2 or 3 and $R^c$ and $R^d$ are independently selected from H, $C_{1-3}$alkyl and $C(O)CH_3$, or, —$C(O)NH$—N=C—$R^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —$CO_2C_{1-3}$alkyl, —$C(O)NH_2$, —OH, $C_{1-3}$alkyl, amino, $C_{1-3}$alkylamino and di$C_{1-3}$ alkylamino;

$R^{10}$ and $R^{11}$ are hydrogen;

$R^{12}$ is selected from =S, oxo, $C_{1-6}$ alkyl, cyano, aminoalkyl, amino, haloalkyl, hydroxyalkyl, =N—$OR^z$, =N—$N(R^z)_2$, wherein $R^z$ is selected from hydrogen or $C_{1-6}$ alkyl; and $R^{13}$ is optionally present and, if present, is selected from from hydrogen, $C_{1-6}$ alkyl, or a halo group.

In yet another embodiment there are provided compounds of formula (I) as described above and wherein X is N;

$R^1$ is hydrogen;

R³ is hydrogen, C₁₋₆ alkyl, amino C₁₋₆ alkyl, hydroxyC₁₋₆ alkyl, cyano C₁₋₆ alkyl, C₃₋₇ cycloalkyl, carbamoyl or CO₂C₁₋₆alkyl; wherein each alkyl, amino, cycloalkyl or carbamoyl group is optionally substituted by $R^x$ wherein $R^x$ can be chosen from:
  hydrogen, amino, C₁₋₆alkyl, C₂₋₆ alkenyl, amino C₁₋₆ alkyl, hydroxy C₁₋₆ alkyl, cyano C₁₋₆ alkyl, C₂₋₆ alkenyl, C₂₋₆ alkynyl, C₁₋₆ alkoxy, C₂₋₆ alkenyloxy, C₂₋₆ alkynyloxy, hydroxy, C₃₋₇ cycloalkyl, acyl, C₃₋₇ cycloalkyl-C₁₋₆ alkyl, C₃₋₇ cycloalkyl-C₂₋₆ alkenyl, carbonyl, carbamoyl, or —CO₂C₁₋₆alkyl;

R⁴ is optionally present and, when present, is selected from hydrogen, or C₁₋₆alkyl;

R⁵ is optionally present and, when present, is hydrogen, C₁₋₆ alkyl or CF₃;

R⁶ is hydrogen, C₁₋₆ alkyl or CF₃; or

R⁵ and R⁶, may optionally be taken together to form a C₃₋₇ cycloalkyl;

R⁷ is hydrogen;

R⁸ is hydrogen;

R⁹ is chosen from hydrogen, C₁₋₆ alkyl, piperidinyl, phenyl, heteroaryl selected from pyridyl, quinolinyl, thiazolyl, indolyl, benzothiazolyl, benzoxazolyl, isoxazolyl, pyrazinyl, pyrimidinyl, benzimidazolyl, oxazolyl, pyrazolyl, 1,3,4-thiadiazolyl, tetrazolyl, 1,3,4-oxadiazolyl, 1,2,4-triazolyl, imidazolyl, pyrrolyl, thiophene, benzothiophene, furanyl and benzofuran, wherein each phenyl, piperidinyl or heteroaryl may be singly or multiply substituted with $R^y$, wherein $R^y$ may be chosen from:
  halogen, C₁₋₆ alkyl, C₂₋₆ alkenyl, C₁₋₆ alkoxy, hydroxy, C₃₋₇ cycloalkyl, phenyl, phenoxy, acyl, —OCF₃, amino, C₁₋₃alkylamino, diC₁₋₃alkylamino, acylamino, hydroxyethylamino, —CN, —CO₂C₁₋₃alkyl, —CH₂NH₂ or —C(O)N($R^a$)($R^b$) where $R^a$ and $R^b$ are independently selected from
  H, C₁₋₃alkyl, —CH₂C(O)NH₂, —(CH₂)ₙOH and —(CH₂)ₙNR^cR^d, where n=2 or 3 and $R^c$ and $R^d$ are independently selected from H, C₁₋₃alkyl and C(O)CH₃, and —C(O)NH—N=C—$R^e$, where $R^e$ is phenyl, or
  $R^a$ and $R^b$ together with the N they are connected to can form a pyrrolidine, piperazine, piperidine or morpholine ring optionally substituted with one to three groups selected from —CO₂C₁₋₃alkyl, —C(O)NH₂, —OH, C₁₋₃alkyl, amino, C₁₋₃alkylamino and diC₁₋₃ alkylamino;

R¹⁰ and R¹¹ are hydrogen; and

R¹² is oxo.

The following are representative examples of the invention which can be made according to the general scheme and working examples below:

TABLE 1

Compound Structures and Names

| Structure | Name |
|---|---|
| | 1-Oxo-1,2,3,4-tetrahydro-pyrazino[1,2-α]indole-7-carboxylic acid pyridin-3-ylamide |
| | 1-Oxo-1,2,3,4-tetrahydro-pyrazino[1,2-α]indole-7-carboxylic acid quinolin-3-ylamide |
| | 4-Methyl-1-oxo-1,2,3,4-tetrahydro-pyrazino[1,2-α]indole-7-carboxylic acid pyridin-3-ylamide |
| | 4-Methyl-1-oxo-1,2,3,4-tetrahydro-pyrazino[1,2-α]indole-7-carboxylic acid quinolin-3-ylamide |

TABLE 1-continued

Compound Structures and Names

| Structure | Name |
|---|---|
| | 4-Methyl-1-oxo-1,2,3,4-tetrahydro-pyrazino[1,2-α]indole-7-carboxylic acid (3-cyano-phenyl)-amide |
| | 1-Oxo-1,2,3,4-tetrahydro-pyrazino[1,2-α]indole-7-carboxylic acid (3-cyano-phenyl)-amide |
| | 1-Oxo-1,2,3,4-tetrahydro-pyrazino[1,2-α]indole-7-carboxylic acid thiazol-2-ylamide |
| | 4-Methyl-1-oxo-1,2,3,4-tetrahydro-pyrazino[1,2-α]indole-7-carboxylic acid thiazol-2-ylamide |
| | (S)-3-Aminomethyl-1-oxo-1,2,3,4-tetrahydro-pyrazino[1,2-α]indole-7-carboxylic acid pyridin-3-ylamide |
| | (S)-3-Aminomethyl-1-oxo-1,2,3,4-tetrahydro-pyrazino[1,2-α]indole-7-carboxylic acid quinolin-3-ylamide |
| | (S)-3-Aminomethyl-1-oxo-1,2,3,4-tetrahydro-pyrazino[1,2-α]indole-7-carboxylic acid thiazol-2-ylamide |

TABLE 1-continued

Compound Structures and Names

| Structure | Name |
|---|---|
| | (R)-3-Aminomethyl-1-oxo-1,2,3,4-tetrahydro-pyrazino[1,2-α]indole-7-carboxylic acid thiazol-2-ylamide |
| | (R)-3-Aminomethyl-1-oxo-1,2,3,4-tetrahydro-pyrazino[1,2-α]indole-7-carboxylic acid (3-cyano-phenyl)-amide |
| | (R)-3-Aminomethyl-1-oxo-1,2,3,4-tetrahydro-pyrazino[1,2-α]indole-7-carboxylic acid quinolin-3-ylamide |
| | (R)-3-Aminomethyl-1-oxo-1,2,3,4-tetrahydro-pyrazino[1,2-α]indole-7-carboxylic acid pyridin-3-ylamide |
| | 9-Oxo-6,7,8,9-tetrahydro-pyrido[1,2-a]indole-3-carboxylic acid pyridin-3-ylamide |
| | 9-Hydroxyimino-6,7,8,9-tetrahydro-pyrido[1,2-a]indole-3-carboxylic acid pyridin-3-ylamide |
| | 4,4-Dimethyl-1-oxo-1,2,3,4-tetrahydro-pyrazino[1,2-a]indole-7-carboxylic acid pyridin-3-ylamide |
| | 4,4-Dimethyl-1-oxo-1,2,3,4-tetrahydro-pyrazino[1,2-a]indole-7-carboxylic acid thiazol-2-ylamide |

TABLE 1-continued

Compound Structures and Names

4-Methyl-1-oxo-1,2,3,4-tetrahydro-pyrazino[1,2-α]indole-7-carboxylic acid pyrazin-2-ylamide 4-Methyl-1-oxo-1,2,3,4-tetrahydro-pyrazino[1,2-α]indole-7-carboxylic acid (4-carbamoyl-3-fluoro-phenyl)-amide 4-Methyl-1-oxo-1,2,3,4-tetrahydro-pyrazino[1,2-α]indole-7-carboxylic acid (5-bromo-pyridin-3-yl)-amide 4-Methyl-1-oxo-1,2,3,4-tetrahydro-pyrazino[1,2-α]indole-7-carboxylic acid (6-acetylamino-pyridin-3-yl)-amide 4-Methyl-1-oxo-1,2,3,4-tetrahydro-pyrazino[1,2-α]indole-7-carboxylic acid benzothiazol-2-ylamide 4-Methyl-1-oxo-1,2,3,4-tetrahydro-pyrazino[1,2-α]indole-7-carboxylic acid (4-carbamoyl-phenyl)-amide 4-Methyl-1-oxo-1,2,3,4-tetrahydro-pyrazino[1,2-α]indole-7-carboxylic acid (4-fluoro-phenyl)-amide 4-Methyl-1-oxo-1,2,3,4-tetrahydro-pyrazino[1,2-α]indole-7-carboxylic acid (4-bromo-phenyl)-amide TABLE 1-continued

| Compound Structures and Names | |
|---|---|
| | 4-Methyl-1-oxo-1,2,3,4-tetrahydro-pyrazino[1,2-α-H6]indole-7-carboxylic acid (3-carbamoyl-phenyl)-amide |
| | 4-Methyl-1-oxo-1,2,3,4-tetrahydro-pyrazino[1,2-α]indole-7-carboxylic acid (3-fluoro-phenyl)-amide |
| | 4-Methyl-1-oxo-1,2,3,4-tetrahydro-pyrazino[1,2-α]indole-7-carboxylic acid (3-bromo-phenyl)-amide |
| | 4-Methyl-1-oxo-1,2,3,4-tetrahydro-pyrazino[1,2-α]indole-7-carboxylic acid (2-carbamoyl-phenyl)-amide |
| | 4-Methyl-1-oxo-1,2,3,4-tetrahydro-pyrazino[1,2-α]indole-7-carboxylic acid (4-cyano-phenyl)-amide |
| | 4-Methyl-1-oxo-1,2,3,4-tetrahydro-pyrazino[1,2-α]indole-7-carboxylic acid (2-fluoro-phenyl)-amide |
| | 4-Methyl-1-oxo-1,2,3,4-tetrahydro-pyrazino[1,2-α]indole-7-carboxylic acid (6-methoxy-pyridin-3-yl)-amide |
| | 4-Methyl-1-oxo-1,2,3,4-tetrahydro-pyrazino[1,2-α]indole-7-carboxylic acid (4-acetylamino-phenyl)-amide |

TABLE 1-continued

Compound Structures and Names

4-Methyl-1-oxo-1,2,3,4-tetrahydro-pyrazino[1,2-α]indole-7-carboxylic acid phenylamide 4-Methyl-1-oxo-1,2,3,4-tetrahydro-pyrazino[1,2-α]indole-7-carboxylic acid (4-carbamoyl-3-chloro-phenyl)-amide 4-Methyl-1-oxo-1,2,3,4-tetrahydro-pyrazino[1,2-α]indole-7-carboxylic acid (3-methoxy-phenyl)-amide 4-Methyl-1-oxo-1,2,3,4-tetrahydro-pyrazino[1,2-α]indole-7-carboxylic acid (3-chloro-phenyl)-amide 4-Methyl-1-oxo-1,2,3,4-tetrahydro-pyrazino[1,2-α]indole-7-carboxylic acid (4-methoxy-phenyl)-amide 4-Methyl-1-oxo-1,2,3,4-tetrahydro-pyrazino[1,2-α]indole-7-carboxylic acid (4-methyl-thiazol-2-yl)-amide 4-Methyl-1-oxo-1,2,3,4-tetrahydro-pyrazino[1,2-α]indole-7-carboxylic acid (6-cyano-pyridin-3-yl)-amide 4-Methyl-1-oxo-1,2,3,4-tetrahydro-pyrazino[1,2-α]indole-7-carboxylic acid (3-ethynyl-phenyl)-amide TABLE 1-continued Compound Structures and Names 4-Methyl-1-oxo-1,2,3,4-tetrahydro-
pyrazino[1,2-α]indole-7-carboxylic acid
(6-carbamoyl-pyridin-3-yl)-amide 4-Methyl-1-oxo-1,2,3,4-tetrahydro-
pyrazino[1,2-α]indole-7-carboxylic acid
(4-acetylamino-3-cyano-phenyl)-amide 1-Oxo-1,2,3,4-tetrahydro-pyrazino[1,2-
a]indole-7-carboxylic acid phenylamide 4-Methyl-1-oxo-1,2,3,4-tetrahydro-
pyrazino[1,2-α]indole-7-carboxylic acid
[4-(2-dimethylamino-ethylcarbamoyl)-
phenyl]-amide 4-Methyl-1-oxo-1,2,3,4-tetrahydro-
pyrazino[1,2-α]indole-7-carboxylic acid
[4-(2-dimethylamino-ethylcarbamoyl)-
3-fluoro-phenyl]-amide 4-Methyl-1-oxo-1,2,3,4-tetrahydro-
pyrazino[1,2-α]indole-7-carboxylic acid
amide 4-Methyl-1-oxo-3,4-dihydro-1#H!-
pyrazino[1,2-α]indole-2,7-dicarboxylic
acid diamide TABLE 1-continued

| Compound Structures and Names | |
|---|---|
| | 4-Methyl-1-oxo-1,2,3,4-tetrahydro-pyrazino[1,2-α]indole-7-carboxylic acid [1,3,4]thiadiazol-2-ylamide |
| | 4-Methyl-1-oxo-1,2,3,4-tetrahydro-pyrazino[1,2-a]indole-7-carboxylic acid [4-(1H-pyrrol-2-yl)-thiazol-2-yl]-amide |
| | 4-Methyl-1-oxo-1,2,3,4-tetrahydro-pyrazino[1,2-a]indole-7-carboxylic acid [4-(5-phenyl-2H-[1,2,4]triazol-3-yl)-thiazol-2-yl]-amide |
| | 4-Methyl-1-oxo-1,2,3,4-tetrahydro-pyrazino[1,2-a]indole-7-carboxylic acid biphenyl-3-ylamide |
| | 4-Methyl-1-oxo-1,2,3,4-tetrahydro-pyrazino[1,2-a]indole-7-carboxylic acid (3'-cyano-biphenyl-3-yl)-amide |

TABLE 1-continued

Compound Structures and Names

4-Methyl-1-oxo-1,2,3,4-tetrahydro-pyrazino[1,2-a]indole-7-carboxylic acid (4'-methyl-biphenyl-3-yl)-amide 4-Methyl-1-oxo-1,2,3,4-tetrahydro-pyrazino[1,2-a]indole-7-carboxylic acid (3'-methoxy-biphenyl-3-yl)-amide 4-Methyl-1-oxo-1,2,3,4-tetrahydro-pyrazino[1,2-a]indole-7-carboxylic acid [3-(1-trityl-1H-imidazol-4-yl)-phenyl]-amide 4-Methyl-1-oxo-1,2,3,4-tetrahydro-pyrazino[1,2-a]indole-7-carboxylic acid (5-methyl-2-phenyl-2H-pyrazol-3-yl)-amide TABLE 1-continued Compound Structures and Names

| Structure | Name |
|---|---|
| | 4-Methyl-1-oxo-1,2,3,4-tetrahydro-pyrazino[1,2-a]indole-7-carboxylic acid (3-pyridin-3-yl-phenyl)-amide |
| | 4-Methyl-1-oxo-1,2,3,4-tetrahydro-pyrazino[1,2-a]indole-7-carboxylic acid (3'-amino-biphenyl-3-yl)-amide |
| | 4-Methyl-1-oxo-1,2,3,4-tetrahydro-pyrazino[1,2-a]indole-7-carboxylic acid (4'-methoxy-biphenyl-3-yl)-amide |
| | 4-Methyl-1-oxo-1,2,3,4-tetrahydro-pyrazino[1,2-a]indole-7-carboxylic acid (2'-methoxy-biphenyl-3-yl)-amide |
| | 4-Methyl-1-oxo-1,2,3,4-tetrahydro-pyrazino[1,2-a]indole-7-carboxylic acid [4-(4-dimethylamino-piperidine-1-carbonyl)-thiazol-2-yl]-amide |

TABLE 1-continued

Compound Structures and Names

| | |
|---|---|
| 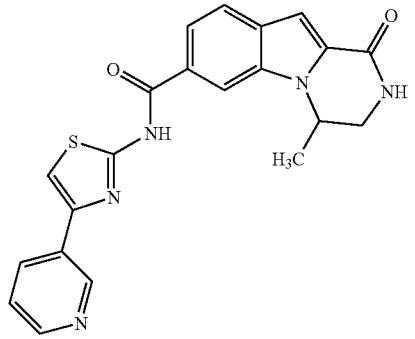 | 4-Methyl-1-oxo-1,2,3,4-tetrahydro-pyrazino[1,2-a]indole-7-carboxylic acid (4-pyridin-3-yl-thiazol-2-yl)-amide |
| 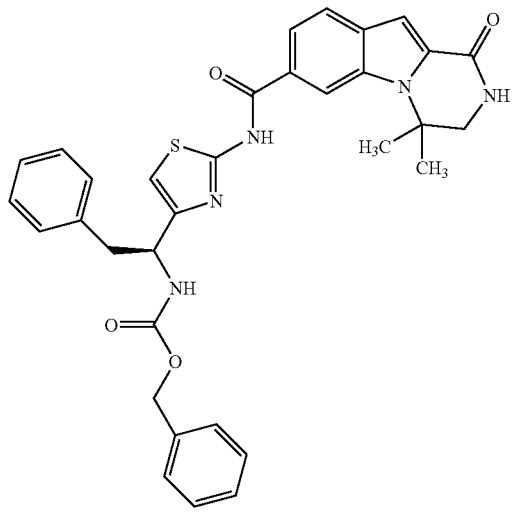 | ((S)-1-{2-[(4,4-Dimethyl-1-oxo-1,2,3,4-tetrahydro-pyrazino[1,2-a]indole-7-carbonyl)-amino]-thiazol-4-yl}-2-phenyl-ethyl)-carbamic acid benzyl ester |
| 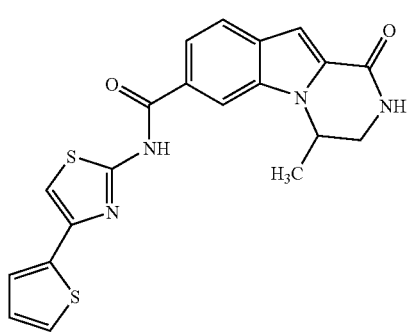 | 4-Methyl-1-oxo-1,2,3,4-tetrahydro-pyrazino[1,2-a]indole-7-carboxylic acid (4-thiophen-2-yl-thiazol-2-yl)-amide |
| 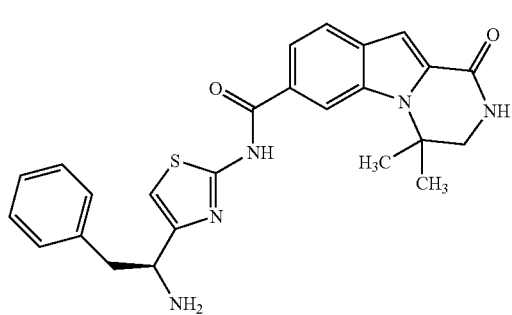 | 4,4-Dimethyl-1-oxo-1,2,3,4-tetrahydro-pyrazino[1,2-a]indole-7-carboxylic acid [4-((S)-1-amino-2-phenyl-ethyl)-thiazol-2-yl]-amide |

TABLE 1-continued

| Compound Structures and Names | |
|---|---|
| | 4-Methyl-1-oxo-1,2,3,4-tetrahydro-pyrazino[1,2-a]indole-7-carboxylic acid [3-(2-methyl-thiazol-4-yl)-phenyl]-amide |
| | 4-Methyl-1-oxo-1,2,3,4-tetrahydro-pyrazino[1,2-a]indole-7-carboxylic acid [3-(1H-imidazol-4-yl)-phenyl]-amide |
| | 4-Methyl-1-oxo-1,2,3,4-tetrahydro-pyrazino[1,2-a]indole-7-carboxylic acid [4-(1-methyl-piperidin-4-ylcarbamoyl)-thiazol-2-yl]-amide |
| | 4-Methyl-1-oxo-1,2,3,4-tetrahydro-pyrazino[1,2-a]indole-7-carboxylic acid [4-(2,2-dimethyl-propylcarbamoyl)-thiazol-2-yl]-amide |

In still another embodiment there are provided preferred compounds according to the present invention having an $IC_{50} \leq 500$:

TABLE 2

| Preferred Compound Structures and Names | |
|---|---|
| | 1-Oxo-1,2,3,4-tetrahydro-pyrazino[1,2-a]indole-7-carboxylic acid quinolin-3-ylamide |
| | 4-Methyl-1-oxo-1,2,3,4-tetrahydro-pyrazino[1,2-a]indole-7-carboxylic acid pyridin-3-ylamide |

TABLE 2-continued

Preferred Compound Structures and Names

| Structure | Name |
|---|---|
| | 4-Methyl-1-oxo-1,2,3,4-tetrahydro-pyrazino[1,2-a]indole-7-carboxylic acid quinolin-3-ylamide |
| | 4-Methyl-1-oxo-1,2,3,4-tetrahydro-pyrazino[1,2-a]indole-7-carboxylic acid (3-cyano-phenyl)-amide |
| | 4-Methyl-1-oxo-1,2,3,4-tetrahydro-pyrazino[1,2-a]indole-7-carboxylic acid thiazol-2-ylamide |
| Chiral | (R)-3-Aminomethyl-1-oxo-1,2,3,4-tetrahydro-pyrazino[1,2-a]indole-7-carboxylic acid thiazol-2-ylamide |
| Chiral | (R)-3-Aminomethyl-1-oxo-1,2,3,4-tetrahydro-pyrazino[1,2-a]indole-7-carboxylic acid (3-cyano-phenyl)-amide |
| Chiral | (R)-3-Aminomethyl-1-oxo-1,2,3,4-tetrahydro-pyrazino[1,2-a]indole-7-carboxylic acid quinolin-3-ylamide |
| Chiral | (R)-3-Aminomethyl-1-oxo-1,2,3,4-tetrahydro-pyrazino[1,2-a]indole-7-carboxylic acid pyridin-3-ylamide |
| | 4,4-Dimethyl-1-oxo-1,2,3,4-tetrahydro-pyrazino[1,2-a]indole-7-carboxylic acid pyridin-3-ylamide |

TABLE 2-continued

Preferred Compound Structures and Names 4,4-Dimethyl-1-oxo-1,2,3,4-tetrahydro-pyrazino[1,2-a]indole-7-carboxylic acid thiazol-2-ylamide 4-Methyl-1-oxo-1,2,3,4-tetrahydro-pyrazino[1,2-a]indole-7-carboxylic acid pyrazin-2-ylamide 4-Methyl-1-oxo-1,2,3,4-tetrahydro-pyrazino[1,2-a]indole-7-carboxylic acid (4-carbamoyl-3-fluoro-phenyl)-amide 4-Methyl-1-oxo-1,2,3,4-tetrahydro-pyrazino[1,2-a]indole-7-carboxylic acid (5-bromo-pyridin-3-yl)-amide 4-Methyl-1-oxo-1,2,3,4-tetrahydro-pyrazino[1,2-a]indole-7-carboxylic acid (6-acetylamino-pyridin-3-yl)-amide 4-Methyl-1-oxo-1,2,3,4-tetrahydro-pyrazino[1,2-a]indole-7-carboxylic acid (3-fluoro-phenyl)-amide 4-Methyl-1-oxo-1,2,3,4-tetrahydro-pyrazino[1,2-a]indole-7-carboxylic acid (4-cyano-phenyl)-amide 4-Methyl-1-oxo-1,2,3,4-tetrahydro-pyrazino[1,2-a]indole-7-carboxylic acid (6-methoxy-pyridin-3-yl)-amide TABLE 2-continued

| Preferred Compound Structures and Names | |
|---|---|
| [structure] | 4-Methyl-1-oxo-1,2,3,4-tetrahydro-pyrazino[1,2-a]indole-7-carboxylic acid (4-carbamoyl-3-chloro-phenyl)-amide |
| [structure] | 4-Methyl-1-oxo-1,2,3,4-tetrahydro-pyrazino[1,2-a]indole-7-carboxylic acid (4-methyl-thiazol-2-yl)-amide |
| [structure] | 4-Methyl-1-oxo-1,2,3,4-tetrahydro-pyrazino[1,2-a]indole-7-carboxylic acid (6-cyano-pyridin-3-yl)-amide |
| [structure] | 4-Methyl-1-oxo-1,2,3,4-tetrahydro-pyrazino[1,2-a]indole-7-carboxylic acid (6-carbamoyl-pyridin-3-yl)-amide |
| [structure] | 4-Methyl-1-oxo-1,2,3,4-tetrahydro-pyrazino[1,2-a]indole-7-carboxylic acid [1,3,4]thiadiazol-2-ylamide |
| [structure] | 4-Methyl-1-oxo-1,2,3,4-tetrahydro-pyrazino[1,2-a]indole-7-carboxylic acid [4-(1H-pyrrol-2-yl)-thiazol-2-yl]-amide |
| [structure] | 4-Methyl-1-oxo-1,2,3,4-tetrahydro-pyrazino[1,2-a]indole-7-carboxylic acid [4-(1-methyl-piperidin-4-ylcarbamoyl)-thiazol-2-yl]-amide |

TABLE 2-continued

Preferred Compound Structures and Names

4-Methyl-1-oxo-1,2,3,4-tetrahydro-pyrazino[1,2-a]indole-7-carboxylic acid [4-(2,2-dimethyl-propylcarbamoyl)-thiazol-2-yl]-amide In all the compounds disclosed in this application, in the event the nomenclature is in conflict with the structure, it shall be understood that the compound is defined by the structure.

The invention includes the use of any compounds that contain one or more asymmetric carbon atoms which may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

The term "cycloalkyl" shall be understood to mean an aliphatic hydrocarbon radical containing from three to twelve carbon atoms. Cycloalkyls include hydrocarbon rings containing from three to ten carbon atoms. These cycloalkyls may be either aromatic and non-aromatic ring systems. The non-aromatic ring systems may be mono- or polyunsaturated. Preferred cycloalkyls include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used inerchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-λ4-thiomorpholinyl, 13-oxa-11-aza-tricyclo [7.3.1.0-2,7]trideca-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo [2.2.1]heptanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include aziridinyl, thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic cycloalkyl or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

Terms which are analogs of the above cyclic moieties such as aryloxy or heteroaryl amine shall be understood to mean an aryl, heteroaryl, heterocycle as defined above attached to it's respective group.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine. The definitions "partially or fully halogenated" "substituted by one or more halogen atoms" includes for example, mono, di or tri halo derivatives on one or more carbon atoms. For alkyl, a nonlimiting example would be —CH$_2$CHF$_2$, —CF$_3$ etc.

The term "ureido", the present specification, is having the general formula of either C(O)NR$^x$R$^y$, NHC(O)R$^x$.

The term "carbamoyl", the present specification, is substituent having the general formula C(O)NR$^x$R$^y$ or NHC(O)R$^x$.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C1-C4 alkyl)4+ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

General Synthetic Methods

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. In the schemes below, unless otherwise specified, X and R$^1$-R$^{13}$ in the formulas shown below shall have the meanings defined for these groups in the definition of the formula (I) of the invention, described hereinabove. Intermediates used in the syntheses below are either commercially available or easily prepared by methods known to those skilled in the art. Reaction progress may be monitored by conventional methods such as thin layer chromatography (TLC). Intermediates and products may be purified by methods known in the art, including column chromatography, HPLC or recrystallization.

Compounds of formula I having X=N, R$^1$, R$^3$ and R$^4$=H and R$^{12}$=oxo and R$^2$ and R$^{13}$ not present may be made as described in Scheme I.

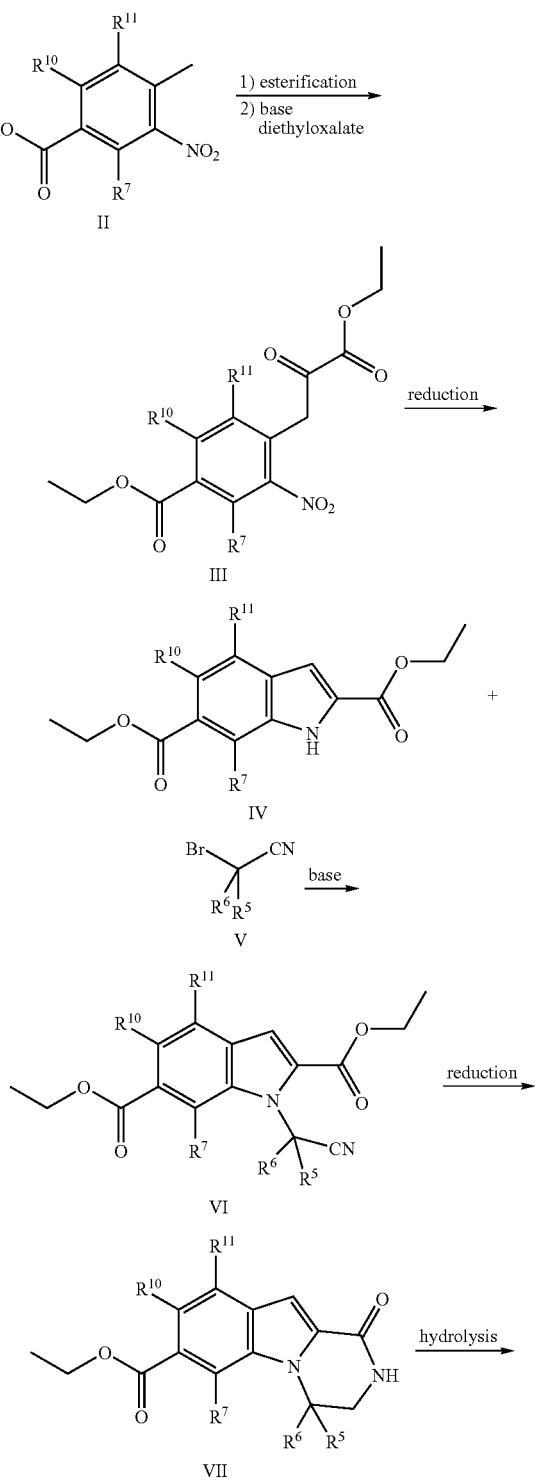

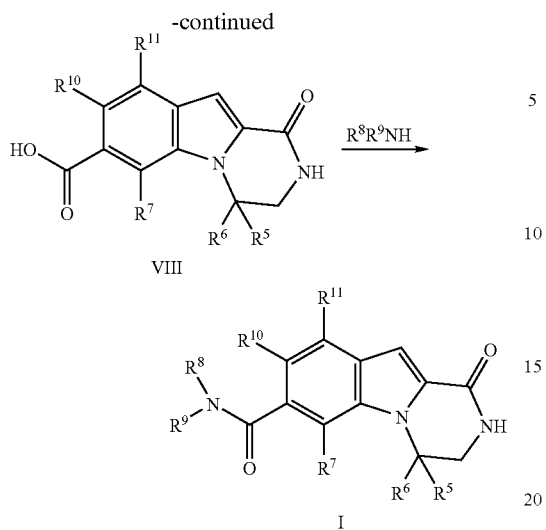

VIII

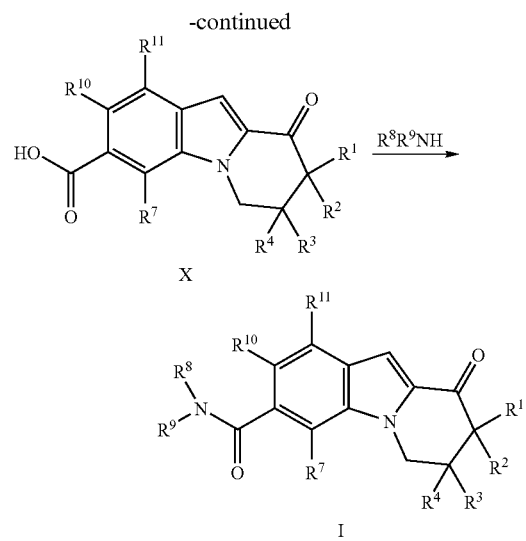

X

I

I

As illustrated in Scheme I, an optionally substituted 3-nitrobenzoic acid (II) is esterified for example by treatment with ethanol in the presence of an acid such as HCl, followed by treatment with diethyloxalate in the presence of a base such as sodium ethoxide in a suitable solvent such as EtOH to provide III. Reduction of III, for example by treatment with zinc metal in acetic acid and water and in situ cyclization provides the indole diester IV. Treatment of IV with an optionally substituted bromoacetonitrile V in the presence of a suitable base such as sodium hydride or potassium carbonate in a suitable solvent such as DMF provides VI. Reduction of the nitrile, for example by treatment with hydrogen in the presence of a suitable catalyst such as $PtO_2$ in a suitable solvent such as EtOH and in situ cyclization provides VII. Hydrolysis of the ester for example by treatment with aqueous base provides VIII. Amide coupling of the carboxylic acid with the desired amine $R^8R^9NH$ provides the desired compound of formula I. Standard peptide coupling reactions known in the art (see for example M. Bodanszky, 1984, The Practice of Peptide Synthesis, Springer-Verlag) may be employed in these syntheses. An example of suitable coupling conditions is treatment of a solution of VIII in a suitable solvent such as DMF with HATU, HOAt, and a base such as diisopropylethylamine, followed by the desired amine $R^8R^9NH$. Further modification of the initial product of formula I by methods known in the art and illustrated in the Examples below may be used to prepare additional compounds of formula I.

Compounds of formula I having X═C and $R^5$ and $R^6$═H, $R^{12}$═oxo and $R^{13}$ not present may be prepared as described in Scheme 2.

Scheme II

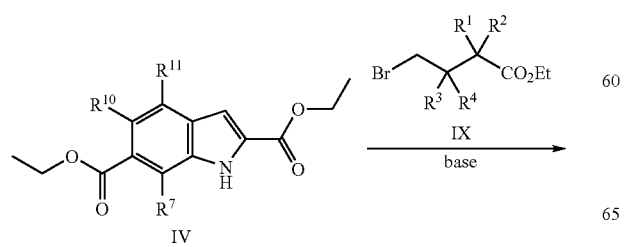

As illustrated in Scheme 2 an indole diester of formula IV (see Scheme I) is treated with an optionally substituted haloester, for example a bromoester as shown (IX), in the presence of a base such as sodium hydride in a suitable solvent such as DMF to provide an intermediate triester which undergoes cyclization, hydrolysis and decarboxylation to provide X upon further treatment with a suitable base such as potassium t-butoxide. Amide coupling of X with the desired amine as described in Scheme I provides the desired compound of formula I.

Compounds of formula I having X═C and an aminomethyl group at $R^3$ may be prepared as described in Scheme 3.

Scheme III

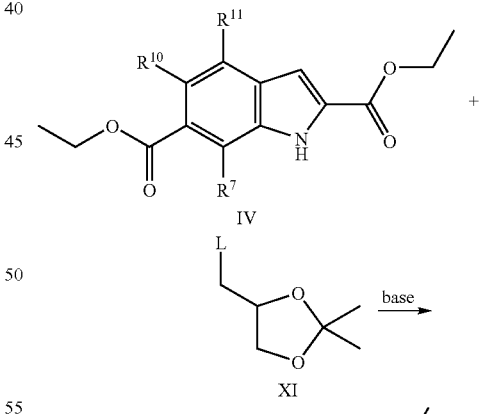

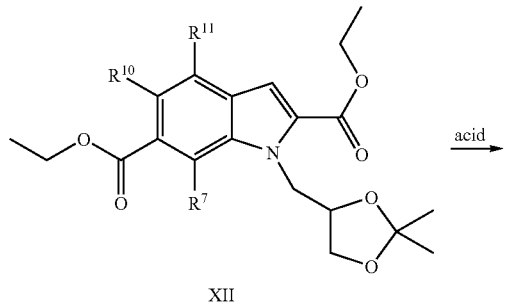

XII

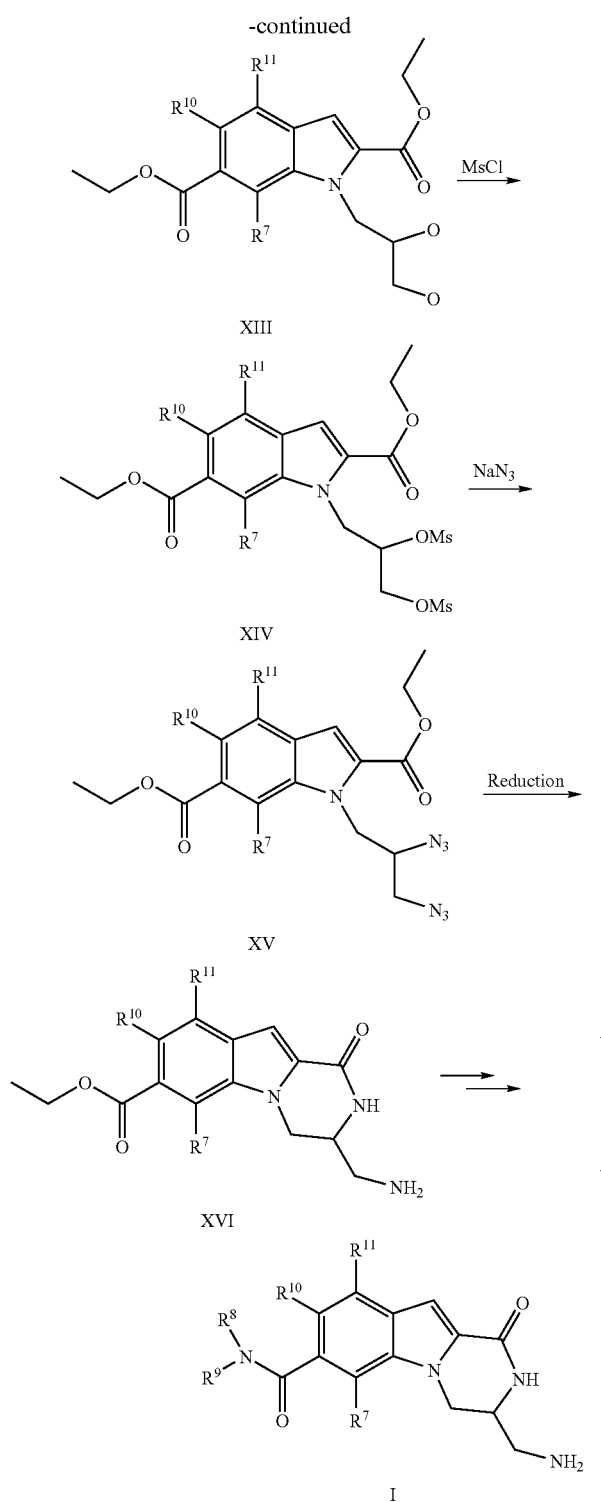

azide in a suitable solvent such as DMF provides the diazide XV. Reduction of the diazide, for example by treatment with trimethylphosphine provides the diamine which cyclizes in situ to provide XVI.

Hydrolysis to the carboxylic acid, protection of the amine for example with a Boc-group, amide coupling as described in Scheme 1 and deprotection of the amine provides the desired compound of formula I having Y=N and aminomethyl at $R^3$.

SYNTHETIC EXAMPLES

Example 1

Synthesis of 4-methyl-1-oxo-1,2,3,4-tetrahydro-pyrazino[1,2-a]indole-7-carboxylic acid pyridin-3-ylamide (1a) and 4-[(4-methyl-1-oxo-1,2,3,4-tetrahydro-pyrazino[1,2-a]indole-7-carbonyl)-amino]-benzoic acid methyl ester (1b)

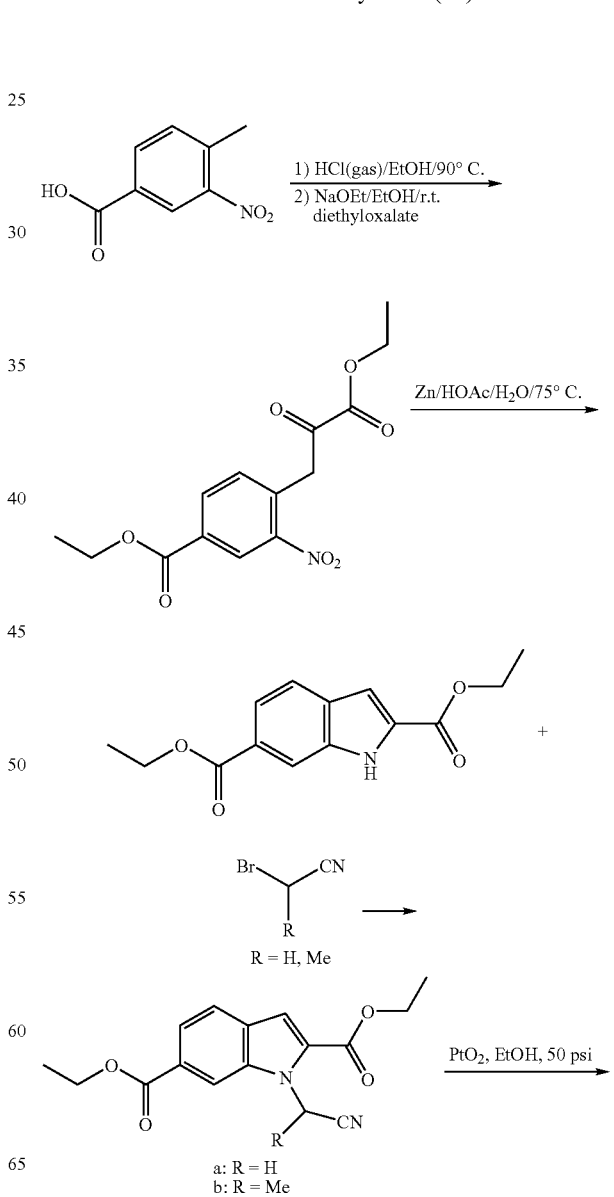

As illustrated above in Scheme III, indole diester IV (see Scheme I) is treated with a ketal such as the 2,2-dimethyl [1,3]dioxolane shown (XI) bearing a methyl group substituted with a leaving group L, for example a tosyl group, in the presence of a base sucgh as potassium carbonate to provide XII. Treatment of the ketal with acid provides diol XIII. Reaction with a sulfonyl chloride such as MsCl as shown provides the disulfonic ester XIV. Treatment with sodium

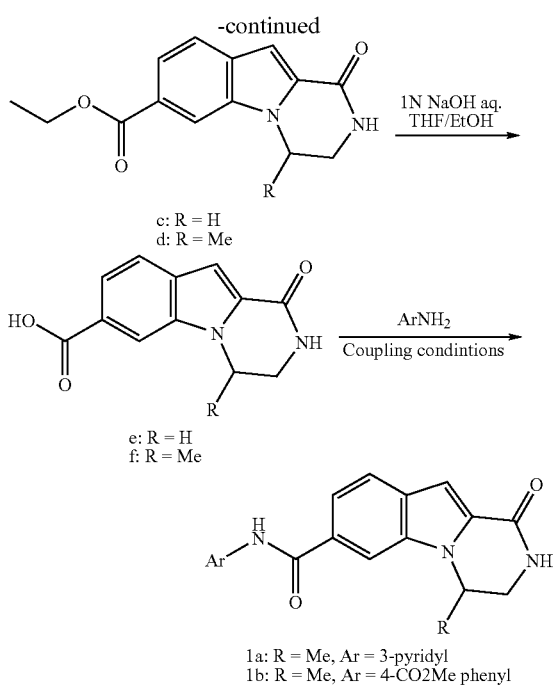

c: R = H
d: R = Me e: R = H
f: R = Me

1a: R = Me, Ar = 3-pyridyl
1b: R = Me, Ar = 4-CO2Me phenyl

4-Methyl-3-nitro-benzoic acid (71 g, 0.39 mol) was dissolved in dry EtOH (600 mL) and dry HCl gas was bubbled into the solution for 5 min. The reaction was heated to 90° C. under $N_2$ for 20 h, then cooled and concentrated to give 4-methyl-3-nitro-benzoic acid ethyl ester as a straw-color liquid (80.0 g, yield 98%).

To a solution of 4-methyl-3-nitro-benzoic acid ethyl ester (80 g, 0.38 mol) and diethyl oxalate (57.13 mL, 0.42 mol) in EtOH (1 L) was added NaOEt (21 wt % in EtOH, 430 mL, 1.15 mol). The resulting brown solution was stirred at room temperature for 16 h.

The reaction was quenched with 3 N HCl and diluted with water (2 L) with cooling and stirring. The resulting white precipitate was filtered off and dried in vacuo to provide 91.1 g of 4-(2-ethoxycarbonyl-2-oxo-ethyl)-3-nitro-benzoic acid ethyl ester, yield 77%.

The above ethyl ester (91 g, 0.29 mol) was suspended in 800 mL of HOAc and the suspension was heated with stirring to 75° C. Once the solids had dissolved, water was added. Zinc dust (189.63 g, 2.9 mmol) was added carefully in a portion-wise manner, keeping the reaction temperature below 85° C. Once the zinc was added, the mixture was stirred vigorously for an additional hour, then EtOAc (1.5 L) was added to dissolve most of the precipitate. The mixture was then filtered through diatomaceous earth, washing with EtOAc (1.5 L). The filtrate was washed twice with water (1.5 L), four times with saturated $NaHCO_3$ (1 L), and once with brine (1 L). The solution was dried with $Na_2SO_4$, filtered, and concentrated to provide a yellow powder. Recrystallization from toluene provided 44.6 g of 1H-indole-2,6-dicarboxylic acid diethyl ester as a yellow powder, yield 58%.

a: 1-Cyanomethyl-1H-indole-2,6-dicarboxylic acid diethyl ester

A mixture of 60% NaH in mineral oil (115 mg, 2.9 mmol) and 1H-indole-2,6-dicarboxylic acid diethyl ester (500 mg, 1.9 mmol) in DMF (3 mL) was stirred at room temperature for 0.5 h. Then bromo-acetonitrile in DMF (1 mL) was added and the reaction was warmed to 77° C. and kept at this temperature overnight. The reaction was cooled and quenched with ice water. A large amount of precipitate formed which was filtered and rinsed with water, followed by cold ether. The wet cake was dried in the vacuum oven (50° C.) to give 585 mg of 1-cyanomethyl-1H-indole-2,6-dicarboxylic acid diethyl ester.

b: 1-(Cyano-methyl-methyl)-1H-indole-2,6-dicarboxylic acid diethyl ester

A mixture of $K_2CO_3$ (7.93 g, 57.0 mmol) and 1H-indole-2,6-dicarboxylic acid diethyl ester (5.0 g, 19.14 mmol) in DMF (30 mL) was stirred at room temperature for 0.5 h. Then 2-bromo-propionitrile (3.4 mL, 38.3 mmol) in DMF (10 mL) was added. The reaction was warmed to 80° C. and kept at this temperature for 6 h. Then the reaction was cooled down to the room temperature. Most of the DMF solvent was removed in vacuo and the crude residue was extracted several times with EtOAc. The combined organic extracts were washed with brine, dried over $MgSO_4$ and concentrated. The crude product was triturated with MeCN to give 3.9 g of 1-(cyano-methyl-methyl)-1H-indole-2,6-dicarboxylic acid diethyl ester as a white fluffy solid. The filtrate was concentrated and purification by silica gel chromatography provided 1.6 g of 1-(cyano-methyl-methyl)-1H-indole-2,6-dicarboxylic acid diethyl ester, yield 91%.

c: 1-Oxo-1,2,3,4-tetrahydro-pyrazino[1,2-a]indole-7-carboxylic acid ethyl ester

To 1-cyanomethyl-1H-indole-2,6-dicarboxylic acid diethyl ester (500 mg, 1.66 mmol) in 20 mL of absolute EtOH was added $PtO_2$ (Adams' catalyst). The reaction mixture was hydrogenated at 50 psi of hydrogen overnight. The reaction mixture was filtered through a pad of diatomaceous earth, the solid cake was washed with dichloromethane several times. The solvent was evaporated to dryness to give 468 mg of 1-oxo-1,2,3,4-tetrahydro-pyrazino[1,2-a]indole-7-carboxylic acid ethyl ester as a light yellow solid.

d: 4-Methyl-1-oxo-1,2,3,4-tetrahydro-pyrazino[1,2-a]indole-7-carboxylic acid ethyl ester 1-(Cyano-methyl-methyl)-1H-indole-2,6-dicarboxylic acid diethyl ester (3.9 g, 12.41 mmol) can be converted to 3.2 g of 4-methyl-1-oxo-1,2,3,4-tetrahydro-pyrazino[1,2-a]indole-7-carboxylic acid ethyl ester following the procedure described above for c.

f: 4-Methyl-1-oxo-1,2,3,4-tetrahydro-pyrazino[1,2-a]indole-7-carboxylic acid

To a suspension of ethyl ester from step d above (3.2 g, 11.75 mmol) in 100 mL of THF/EtOH (1:1 v/v) was added 1 N aq NaOH (43 mL, 43 mmol). The reaction mixture became a clear solution upon addition of 1 N NaOH. The clear solution was heated at 75° C. for 2 h. The reaction was concentrated and the crude residue was dissolved in water, and extracted with ether. The aqueous layer was acidified to pH ~4 with 3 N HCl (~16 mL). A large amount of white precipitate formed which was filtered off and rinsed with cold ether. The wet product was dried in the vacuum oven (50° C.) to provide 2.2 g of 4-Methyl-1-oxo-1,2,3,4-tetrahydro-pyrazino[1,2-a]indole-7-carboxylic acid, yield 77% for two steps.

e: 1-Oxo-1,2,3,4-tetrahydro-pyrazino[1,2-a]indole-7-carboxylic acid

1-Oxo-1,2,3,4-tetrahydro-pyrazino[1,2-a]indole-7-carboxylic acid (468 mg, 1.81 mmol) was obtained from c following the procedure described above for step f, yield 87%.

1a: 4-Methyl-1-oxo-1,2,3,4-tetrahydro-pyrazino[1,2-a]indole-7-carboxylic acid pyridin-3-ylamide To a solution of 4-methyl-1-oxo-1,2,3,4-tetrahydro-pyrazino[1,2-a]indole-7-carboxylic acid (step f) (20 mg, 0.08 mmol) in 1 mL of DMF was added HATU (34.3 mg, 0.082 mmol), HOAt (6, 0.04 mmol) and diisopropylethylamine (29 uL, 0.164 mmol). After 15 min, 3-amino-pyridine in 1 mL of DMF was added. The mixture was stirred at room temperature for 48 h. The reaction was extracted with EtOAc several times, washed with water and brine. The combined organics were dried over $MgSO_4$, filtered, and concentrated in vacuum. Purification by silica gel chromatography gave 23 mg of 4-methyl-1-oxo-1,2,3,4-tetrahydro-pyrazino[1,2-a]indole-7-carboxylic acid pyridin-3-ylamide 87% as a white solid. ESI-MS m/z 321.34 $[M+H]^+$.

1b: 4-[(4-Methyl-1-oxo-1,2,3,4-tetrahydro-pyrazino[1,2-a]indole-7-carbonyl)-amino]-benzoic acid methyl ester Method 1:

To a suspension of 4-methyl-1-oxo-1,2,3,4-tetrahydro-pyrazino[1,2-a]indole-7-carboxylic acid (step f) (50 mg, 0.205 mmol) in dichloromethane (1 mL) at 0° C. was added oxalyl chloride solution in dichloromethane (2.0 M, 113 uL, 0.225 mmol), followed by one drop of DMF to initiate the reaction. The reaction mixture was stirred at room temperature for 15 min and concentrated and dried under vacuum to afford the acid chloride as a yellow oil which was dissolved in dichloromethane (1 mL). Then DMAP (2.5 mg, 0.02 mmol) and diisopropylethylamine (63 uL, 0.36 mmol) were added followed by 4-amino-benzoic acid methyl ester (34 mg, 0.225 mmol). The reaction mixture was stirred at room temperature overnight. The solvent was removed to give a yellow oil which was purified by prep-HPLC to give 4-[(4-Methyl-1-oxo-1,2,3,4-tetrahydro-pyrazino[1,2-a]indole-7-carbonyl)-amino]-benzoic acid methyl ester. ESI-MS m/z 378.39 $[M+H]^+$.

Method 2:

To a suspension of 4-methyl-1-oxo-1,2,3,4-tetrahydro-pyrazino[1,2-a]indole-7-carboxylic acid (step f) (50 mg, 0.205 mmol) in dichloromethane (1 mL) was added (1-chloro-2-methyl-propenyl)-dimethyl-amine (Ghosez's reagent, 34 uL, 0.256 mmol) under argon. The reaction mixture was stirred at room temperature for 2 h and the reaction became a yellow clear solution. The acid chloride formed in situ was characterized by quenching a drop of reaction mixture with MeOH to form the methyl ester (ESI-MS m/z 259 $[M+H]^+$). The clear solution of acid chloride was added to a solution of 4-amino-benzoic acid methyl ester (19.3 mg, 0.128 mmol) and pyridine (10.4 uL, 0.128 mmol) in dichloromethane (300 uL). The orange colored solution was stirred at room temperature for 1 h. Solvents were removed to give crude product which was purified by prep-HPLC to provide 59 mg of 4-[(4-methyl-1-oxo-1,2,3,4-tetrahydro-pyrazino[1,2-a]indole-7-carbonyl)-amino]-benzoic acid methyl ester as white solid, yield 77%. ESI-MS m/z 378.39 $[M+H]^+$.

Example 2

Synthesis of 4-methyl-1-oxo-1,2,3,4-tetrahydro-pyrazino[1,2-a]indole-7-carboxylic acid amide (2a) and 4-methyl-1-oxo-3,4-dihydro-1H-pyrazino[1,2-a]indole-2,7-dicarboxylic acid diamide (2b)

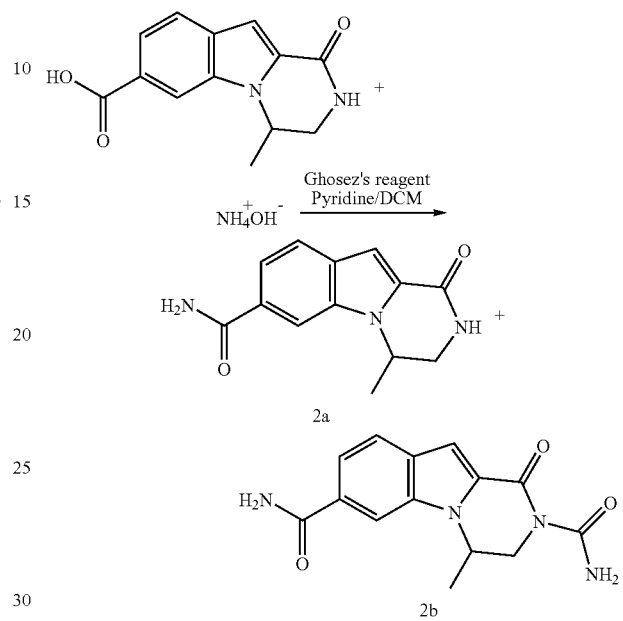

To a suspension of 4-methyl-1-oxo-1,2,3,4-tetrahydro-pyrazino[1,2-a]indole-7-carboxylic acid (Example 1, step f) (25 mg, 0.10 mmol) in dichloromethane (500 uL) at 0° C. was added oxalyl chloride solution in dichloromethane (2.0 M, 102 uL, 0.204 mmol) followed by one drop of DMF to initiate the reaction (bubbling). The ice bath was removed and the reaction stirred at room temperature for 15 min. The reaction was then concentrated to dryness. The resulting yellow oily residue was dissolved in 1 mL of MTBE and 500 uL of dichloromethane to help dissolved, and cooled to 0° C. on an ice-bath. Ammonium hydroxide solution (28% in water, 140 uL, 1.02 mmol) was added drop wise and the reaction mixture was stirred vigorously for 1 h, then concentrated and purified by prep-HPLC to provide 10 mg (yield, 40.2%) of the title compound 2a and 8 mg (yield, 27.3%) of title compound 2b. ESI-MS m/z 244.26 $[M+H]^+$ for compound 2a, m/z 287.29 $[M+H]^+$ for compound 2b.

Example 3

Synthesis of 4-[(4-methyl-1-oxo-1,2,3,4-tetrahydro-pyrazino[1,2-a]indole-7-carbonyl)-amino]-benzoic acid

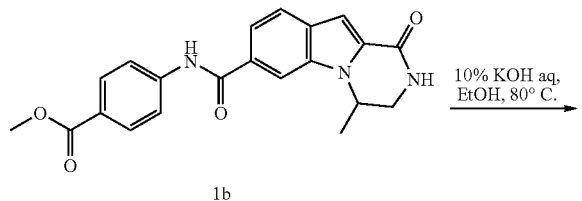

63

-continued

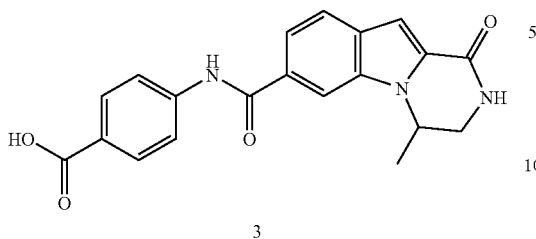

3

To a suspension of 1b (Example 1) (33 mg, 0.09 mmol) in EtOH (2 mL) was added 10% of aqueous KOH (174 uL, 0.35 mmol). The mixture was heated to 80° C. for 3 h. The reaction was cooled to room temperature and concentrated. The resulting residue was dissolved in water (7 mL) and acidified with 6 N HCl to pH ~2. A large amount of white precipitate formed which was filtered and rinsed with ether and dried in the vacuum oven (50° C.) to provide 18 mg of the title compound, yield 57%. ESI-MS m/z 362.37 [M−H]−.

Example 4

Synthesis of 4-methyl-1-oxo-1,2,3,4-tetrahydro-pyrazino[1,2-a]indole-7-carboxylic acid[4-(2-dimethylamino-ethylcarbamoyl)-phenyl]-amide

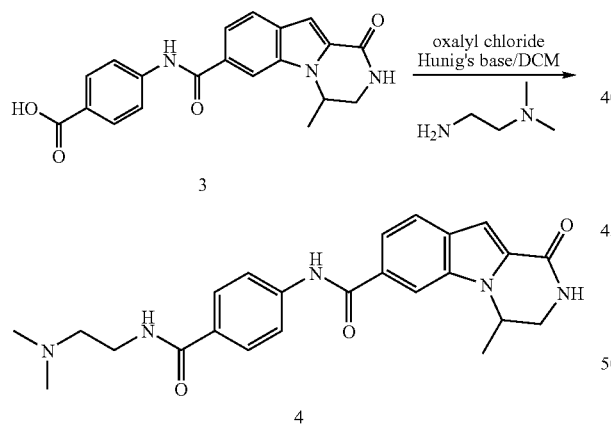

To a suspension of 3 (Example 3) (18 mg, 0.05 mmol) in dichloromethane (500 uL) at 0° C. was added oxalyl chloride solution in dichloromethane (2.0 M, 50 uL, 0.10 mmol), followed by one drop of DMF to initiate the reaction. The reaction mixture was stirred at room temperature for 15 min, concentrated and dried under vacuum to afford the acid chloride as a yellow oil which was dissolved in dichloromethane (1 mL). N,N'-dimethylethylene diamine (18 mg, 0.20 mmol) was added. The reaction mixture was stirred at room temperature overnight. The solvent was removed to give a yellow oil which was purified by prep-HPLC to give 9 mg of the title compound, yield 42%. ESI-MS m/z 434.50 [M+H]+.

64

Example 5

Synthesis of (R)-3-aminomethyl-1-oxo-1,2,3,4-tetrahydro-pyrazino[1,2-a]indole-7-carboxylic acid pyridin-3-ylamide

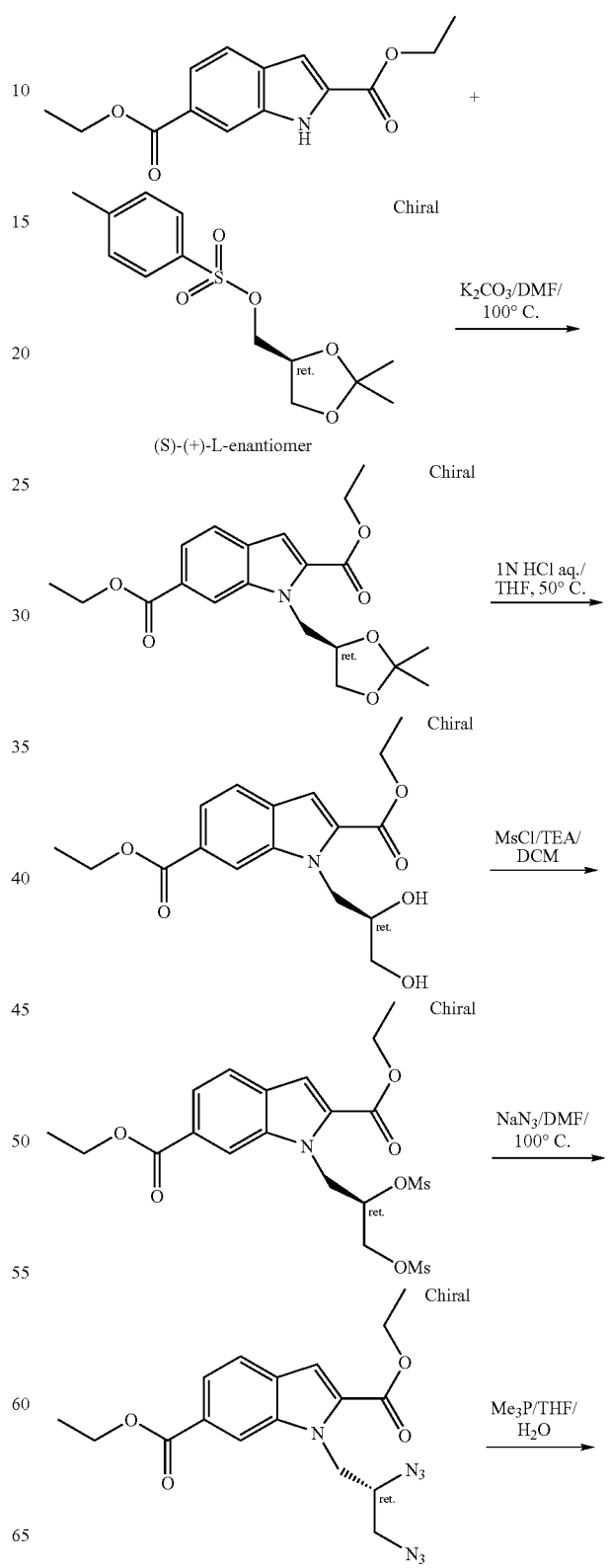

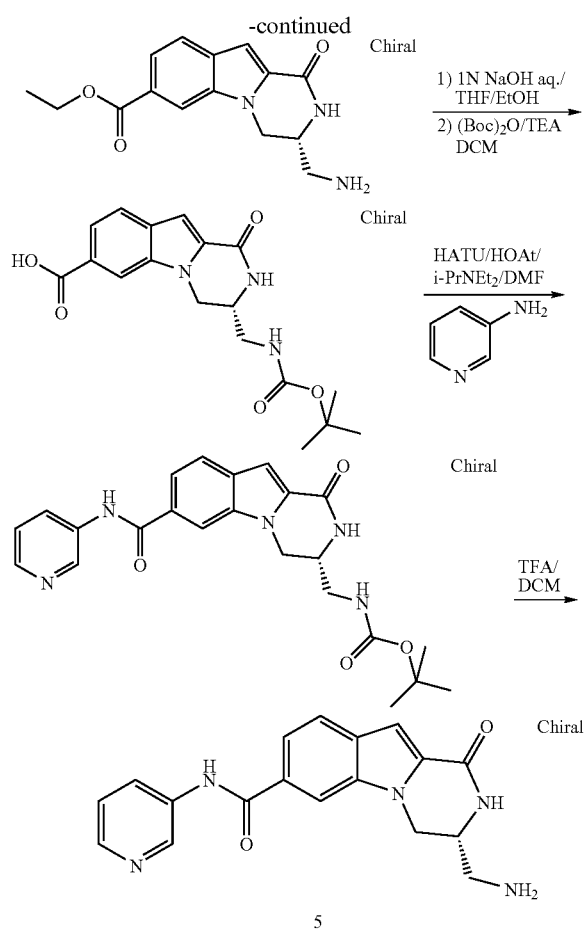

A mixture of K₂CO₃ (1.06 g, 7.65 mmol) and 1H-indole-2,6-dicarboxylic acid diethyl ester (1.0 g, 3.8 mmol) in DMF (15 mL) was stirred at room temperature for 0.5 h. Then toluene-4-sulfonic acid (S)-2,2-dimethyl-[1,3]dioxolan-4-yl methyl ester (1.20 g, 4.2 mmol) in DMF (5 mL) was added. The reaction mixture was warmed to 100° C. and kept at this temperature overnight. The reaction was concentrated and the residues were extracted with EtOAc several times. The combined organic extracts were washed with brine, dried over MgSO₄ and concentrated. Purification by silica gel chromatography gave 1.34 g of 1-((R)-2,2-dimethyl-[1,3]dioxolan-4-ylmethyl)-1H-indole-2,6-dicarboxylic acid diethyl ester as white solid, yield 93%. ESI-MS m/z 376.42 [M+H]⁺.

To a solution of the above diethyl ester (1.34 g, 3.6 mmol) in THF (15 mL) was added 3 N HCl aq. (3.6 mL, 10.7 mmol). The reaction mixture was warmed to 50° C. for 3 h and concentrated in vacuum to give 1.3 g of 1-((R)-2,3-Dihydroxy-propyl)-1H-indole-2,6-dicarboxylic acid diethyl ester as an oil which solidified on standing at room temperature. ESI-MS m/z 336.35 [M+H]⁺.

To a solution of the above diol (1.31 g, 3.91 mmol) and triethylamine (2.72 mL, 19.53 mmol) in dichloromethane (15 mL) was added MsCl (907 uL, 11.72 mmol). The reaction mixture was stirred at room temperature for 4 h, then quenched by water and extracted with dichloromethane several times. The combined organic extracts were washed with brine, dried over MgSO₄ and concentrated to give 1.77 g of 1-((R)-2,3-bis-methanesulfonyloxy-propyl)-1H-indole-2,6-dicarboxylic acid diethyl ester as yellow oil. ESI-MS m/z 492.54 [M+H]⁺.

To a solution of the above dimesylate (1.77 g, 3.60 mmol) in DMF (15 mL) was added NaN₃ (1.4 g, 21.60 mmol). The reaction mixture was warmed to 100° C. overnight. The reaction was concentrated and extracted with EtOAc several times. The combined organic extracts were washed with brine, dried over MgSO₄ and concentrated. Purification by silica gel chromatography gave 896 mg of 1-((S)-2,3-diazido-propyl)-1H-indole-2,6-dicarboxylic acid diethyl ester as colorless oil, yield 64%. ESI-MS m/z 386.38 [M+H]⁺.

To a solution of the above diazide (455 mg, 1.18 mmol) in 10 mL of THF/water (3:1 v/v) was added PMe₃ solution in toluene (1.0 M, 4.72 mL, 4.72 mmol), at room temperature, under Argon. The reaction was complete after 1 h. The milky reaction mixture was concentrated down and the resulting residue was partitioned between EtOAc and water. The majority of product did not completely dissolve in EtOAc. The solid was filtered off and dried in a vacuum oven (50° C.) to give 200 mg of (R)-3-aminomethyl-1-oxo-1,2,3,4-tetrahydro-pyrazino[1,2-a]indole-7-carboxylic acid ethyl ester as a white solid. The organic layer from the EtOAc extraction was dried with MgSO₄, filtered and concentrated to provide 190 mg additional product. ESI-MS m/z 288.31 [M+H]⁺.

To a suspension of the above amine (200 mg, 0.696 mmol) in dichloromethane (3 mL) was added triethylamine (97 uL, 0.7 mmol) followed by (Boc)₂O (152 mg, 0.7 mmol). The reaction mixture was stirred at room temperature for 1 h and concentrated to provide (R)-3-(tert-butoxycarbonylaminomethyl)-1-oxo-1,2,3,4-tetrahydro-pyrazino[1,2-a]indole-7-carboxylic acid ethyl ester as white solid. ESI-MS m/z 388.43 [M+H]⁺.

To a white suspension of the above Boc-protected amine (269 mg, 0.7 mmol) in 8 mL of THF/EtOH (1:1 v/v) was added 1 N NaOH (2.09 mL, 2.1 mmol). The clear solution was warmed at 65° C. for 2 h. The reaction was concentrated, and partitioned between diethyl ether and water. The aqueous layer was acidified with 1 N HCl to ~pH 4. The white precipitate formed was filtered off and dried in the vacuum oven (50° C.) to provide 229 mg of (R)-3-(tert-butoxycarbonylamino-methyl)-1-oxo-1,2,3,4-tetrahydro-pyrazino[1,2-a]indole-7-carboxylic acid as a white solid, yield 92%. ESI-MS m/z 358.38 [M−H]⁻

To a solution of the above carboxylic acid (94 mg, 0.262 mmol) in 2 mL of DMF (2 mL) was added HATU (104.5 mg, 0.275 mmol), HOAt (18.6 mg, 0.137 mmol) and N,N'-diisopropylethylamine (96 uL, 0.55 mmol). After 15 min, 3-amino-pyridine (26 mg, 0.275 mmol) in 1 mL of DMF was added. The reaction mixture was warmed at 80° C. for 8 h. The reaction was concentrated and extracted with EtOAc several times. The combined organic extracts were washed with brine, dried over MgSO₄ and concentrated. Purification by silica gel chromatography gave 73 mg of [(R)-1-oxo-7-(pyridin-3-ylcarbamoyl)-1,2,3,4-tetrahydro-pyrazino[1,2-a]indol-3-ylmethyl]-carbamic acid tert-butyl ester, yield 64%. The product was characterized by ¹H NMR and mass spectroscopy. ESI-MS m/z 436.48 [M+H]⁺.

To a solution of the above ester (28 mg, 0.07 mmol) in dichloromethane (1 mL) was added 50 uL of TFA dropwise. The reaction was stirred at room temperature for 5 h, diluted with toluene (1 mL) and concentrated to give a crude oil which was dissolved in MeOH and concentrated to form a yellow oil again. Upon addition of MeCN/MeOH, a precipitate forms. The solvent was carefully removed by rotary evaporation without warming to provide a yellow foam which was dried in the vacuum oven (50° C.). 32 mg of the title compound was isolated as the 2TFA salt, yield 89%. ESI-MS m/z 336.36 [M+H]+

Example 6

Synthesis of 9-oxo-6,7,8,9-tetrahydro-pyrido[1,2-a]indole-3-carboxylic acid pyridin-3-ylamide

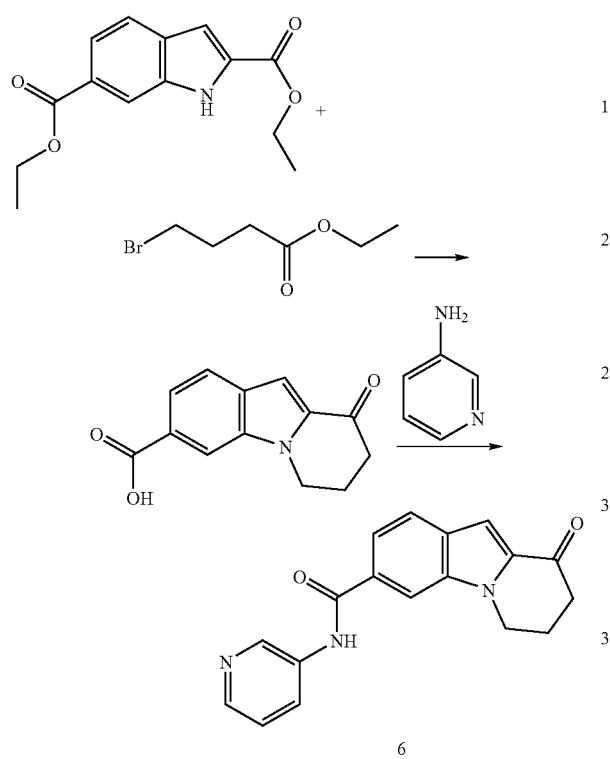

6

To a stirred suspension of NaH (260 mg of 60 wt % in mineral oil, 6.50 mmol) in DMF (5 mL) under an atmosphere of dry nitrogen was added 1H-indole-2,6-dicarboxylic acid diethyl ester (see Example 1) (1.50 g, 5.74 mmol) in DMF (40 mL) over 5 min. Ethyl 4-bromobutyrate (1.40 g, 7.2 mmol) was added dropwise, and the reaction was stirred at room temperature for 20 h. The reaction was quenched with water and extracted into methylene chloride (3×50 mL). The combined organic extracts were washed with brine, dried over MgSO4, and concentrated. The crude tri-ester intermediate was taken up in dry THF (30 mL) and to this solution was added potassium tert-butoxide (20 mL of a 1.0 M solution in THF, 20 mmol). After stirring at room temperature for 16 h, the reaction was quenched with water (60 mL) and concentrated HCl (75 mL) and refluxed for 5 h. The resulting suspension was cooled, filtered, then washed with water followed by hexanes. The resulting solid was dried in a vacuum oven to give 9-oxo-6,7,8,9-tetrahydro-pyrido[1,2-a]indole-3-carboxylic acid (1.25 g, 95%) as an analytically pure purple powder.

To a solution of 9-oxo-6,7,8,9-tetrahydro-pyrido[1,2-a]indole-3-carboxylic acid (983 mg, 4.29 mmol) in anhydrous DMF (5 mL) was added HATU (4.00 g, 10.5 mmol), DMAP (3.00 g, 25.0 mmol) and pyridine-3-ylamine (1.00 g, 10.6 mmol). The reaction was stirred at 65° C. for 36 h. The reaction was poured into water and the resulting precipitate was filtered, washed with water and triturated with cold MeCN to give the title compound (256 mg, 20%) as an analytically pure as a brown powder; ESI-MS m/z 306 [M+H]+.

Example 7

Synthesis of 9-hydroxyimino-6,7,8,9-tetrahydro-pyrido[1,2-a]indole-3-carboxylic acid pyridin-3-ylamide

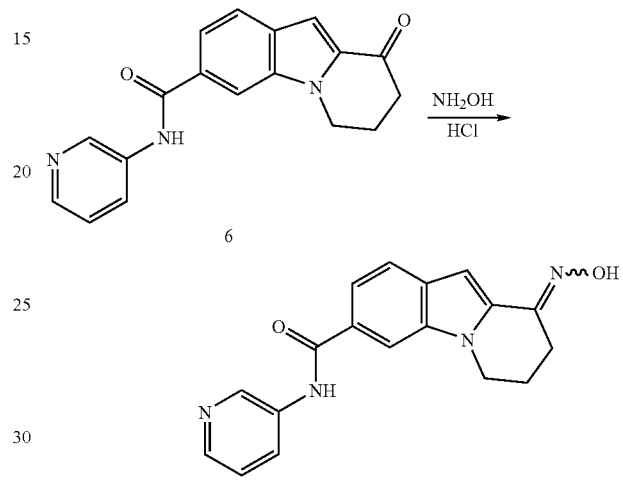

6

7

9-Oxo-6,7,8,9-tetrahydro-pyrido[1,2-a]indole-3-carboxylic acid pyridin-3-ylamide (150 mg, 0.491 mmol), hydroxylamine hydrochloride (1.50 g, 21.6 mmol), and pyridine (3 mL) were combined in MeOH (40 mL) and heated to 60 □C for 20 h. The reaction was cooled and diluted with water (200 mL). The resulting precipitate was filtered, washed with water, then hexanes, and dried in a vacuum oven to give the title compound (122 mg, 78%) as an analytically pure mixture of oxime regioisomers (2:1).

Example 8

Synthesis of 4,4-dimethyl-1-oxo-1,2,3,4-tetrahydro-pyrazino[1,2-a]indole-7-carboxylic acid pyridin-3-ylamide

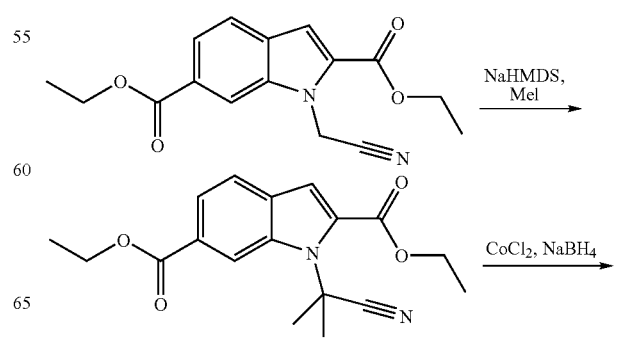

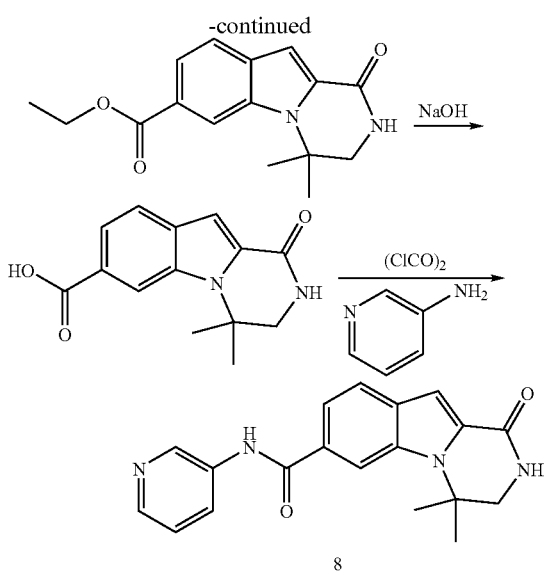

1-Cyanomethyl-1H-indole-2,6-dicarboxylic acid diethyl ester (348 mg, 1.16 mmol) was dissolved in 15 mL of THF and the solution was chilled to 0° C. Iodomethane (0.29 mL, 4.6 mmol) was added followed by the slow addition of 3.48 mL (3.48 mmol) of 1.0 M NaHMDS in THF. The mixture was stirred overnight. The mixture was partitioned between EtOAc and saturated NH$_4$Cl, and then the EtOAc was washed with water and brine, and the washes were extracted once with EtOAc. The combined extracts were dried (Na$_2$SO$_4$), filtered, concentrated, and chromatographed (20-50% EtOAc in hexanes) to provide 238 mg of 1-(cyano-dimethyl-methyl)-1H-indole-2,6-dicarboxylic acid diethyl ester.

1-(Cyano-dimethyl-methyl)-1H-indole-2,6-dicarboxylic acid diethyl ester (238, 0.725 mmol) was suspended in 3 mL of MeOH and 2 mL of THF, and 188 mg (1.45 mmol) of CoCl$_2$ was added. While the mixture was stirred in a 0° C. bath, 274 mg (7.25 mmol) of NaBH$_4$ was carefully added in small portions. The cold bath was removed and the mixture was stirred for 30 min. The vessel was sealed and heated to 60° C. with stirring for 4 h. The mixture was cooled and partitioned between EtOAc and saturated aqueous NaHCO$_3$. The organic phase was then washed with 1 M NaHSO$_4$ and brine, dried with Na$_2$SO$_4$, filtered, and concentrated. The residue was chromatographed (1-5% MeOH in CH$_2$Cl$_2$) to provided 65 mg of 4,4-dimethyl-1-oxo-1,2,3,4-tetrahydro-pyrazino[1,2-a]indole-7-carboxylic acid ethyl ester. ESI-MS m/z 287 [M+H]$^+$.

A 3M aqueous solution of NaOH (0.27 mL) was added to 58 mg (0.20 mmol) of 4,4-dimethyl-1-oxo-1,2,3,4-tetrahydro-pyrazino[1,2-a]indole-7-carboxylic acid ethyl ester in 5 mL of EtOH. After 3 h an additional 0.27 mL of NaOH (3M) was added followed by 1 mL of H$_2$O, and the mixture was heated to 50° C. for 3 h. The mixture was diluted with water, chilled to 0° C., and concentrated HCl was added until the pH reached 2. The resulting suspension was stirred for 1 h at 0° C. then filtered and washed with water. The filter was dried in the vacuum oven at 60° C. overnight to provide 51 mg of 4,4-dimethyl-1-oxo-1,2,3,4-tetrahydro-pyrazino[1,2-a]indole-7-carboxylic acid.

To a suspension of 24 mg (0.093 mmol) of 4,4-dimethyl-1-oxo-1,2,3,4-tetrahydro-pyrazino[1,2-a]indole-7-carboxylic acid in 2:1 CH$_2$Cl$_2$/THF (3 mL) was added 16 μL (0.19 mmol) oxalyl chloride followed by two drops of 10% DMF in THF. After stirring for 1 h, the mixture was concentrated and 1 mL of CH$_2$Cl$_2$ was added followed by 17 mg (0.19 mmol) of 3-aminopyridine and 33 μL (0.19) of diisopropylethylamine. The mixture was stirred overnight, concentrated, and chromatographed (0-8% MeOH in CH$_2$Cl$_2$) to provide 30 mg of the title compound. ESI-MS m/z 3335 [M+H]$^+$.

Example 9

Synthesis of 4,4-dimethyl-1-oxo-1,2,3,4-tetrahydro-pyrazino[1,2-a]indole-7-carboxylic acid thiazol-2-ylamide

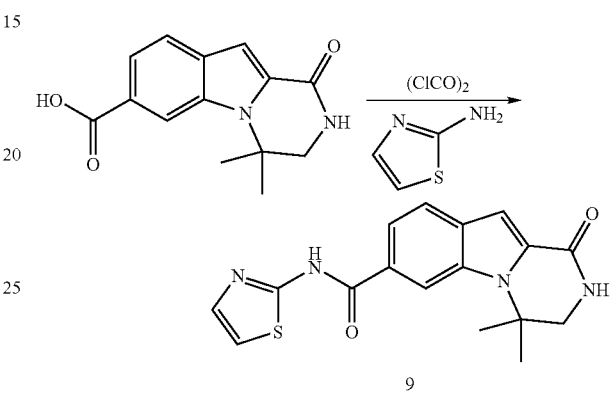

To a suspension of 24 mg (0.093 mmol) of 4,4-dimethyl-1-oxo-1,2,3,4-tetrahydro-pyrazino[1,2-a]indole-7-carboxylic acid in 2:1 CH$_2$Cl$_2$/THF (3 mL) was added 16 μL (0.19 mmol) oxalyl chloride followed by two drops of 10% DMF in THF. After stirring for 1 h, the mixture was concentrated and 1 mL of CH$_2$Cl$_2$ was added followed by 19 mg (0.19 mmol) of 2-aminothiazole and 22 μL (0.19 mmol) of 2,6-lutidine. The mixture was stirred overnight, concentrated, and chromatographed (0-8% MeOH in CH$_2$Cl$_2$) to provide 17 mg of the title compound. ESI-MS m/z 340.9 [M+H]$^+$.

Procedure for the Identification of MAPKAP-k2 Inhibitors

The protein reagents required for the phosphoryl transfer reaction catalyzed by MAPKAP-k2 include 1 nM MAPKAP-k2 (1-400) and 500 nM biotinylated LSP1 (179-339). The MAPKAP-k2 (1-400) splice variant used in the reaction is expressed as an amino-terminal glutathione transferase fusion protein in insect cells, purified by glutathione affinity chromatography and activated with murine p38α (Lukas et al., (2004) Biochemistry 43, 9950-9960). The biotinylated LSP1 (179-339) is prepared from an amino-terminal GST fusion of the carboxy-terminal portion of lymphocyte specific protein 1 (LSP1 179-339), expressed in *E. coli* and purified by glutathione affinity chromatography (Lukas et al., (2004) Biochemistry 43, 9950-9960). LSP1 (179-339) is covalently modified with iodoacetyl biotin (Pierce Chemicals). The phosphoryl transfer reaction (30 min) is performed in Reacti-Bind NeutrAvidin Coated plates (Pierce Chemicals) in buffer containing 50 mM HEPES (pH 7.6), 50 mM KCl, 10 mM MgCl$_2$, 100 μM Na$_3$VO$_4$, 0.01% CHAPS, 1 mM DTT, 10 μg/mL bovine serum albumin, 2 μM ATP, 0-30 μM compound and 1-2% DMSO (v/v).

The protein reagent required for detection of MAPKAP-k2 (1-400) dependent phosphorylation of biotinylated LSP1 (179-339) and inhibitors of MAPKAP-k2 (1-400) catalysis is Eu$^{3+}$ chelated anti-phospho-LSP1 IgG1 monoclonal antibody. The anti-phospho-LSP1 IgG$_1$ monoclonal antibody is raised against the following amino acid sequence: CRTP-KLARQA(phospho-S)IELPSM (Anaspec) conjugated to KLH antigen from Pierce Chemicals. The antibody is covalently modified with Eu N1 ITC Chelate from Perkin Elmer Life Sciences. The detection of MAPKAP-k2 (1-400) dependent phosphorylation of LSP1 (179-339) and inhibitors of MAPKAP-k2 (1-400) catalysis is performed by (1) washing the Reacti-Bind NeutrAvidin Coated plates with Delfia Wash Buffer (Perkin Elmer Life Sciences), (2) adding the $Eu^{3+}$ chelated anti-phospho-LSP1 IgG1 monoclonal antibody to the Reacti-Bind NeutrAvidin Coated plates (1 hr), (3) washing the Reacti-Bind NeutrAvidin Coated plates with Delfia Wash Buffer, (4) adding Delfia Enhancement Solution (15 min) from Perkin Elmer Life Sciences, and (5) reading time resolved fluorescence with an excitation maximum of 360 nm and an emission maximum of 620 nm on an LJL Biosystems Analyst instrument.

Inhibition of TNF Production in THP Cells

The inhibition of cytokine production can be observed by measuring inhibition of TNFα in lipopolysaccharide stimulated THP cells (for example, see W. Prichett et al., 1995, *J. Inflammation,* 45, 97). All cells and reagents were diluted in RPMI 1640 with phenol red and L-glutamine, supplemented with additional L-glutamine (total: 4 mM), penicillin and streptomycin (50 units/ml each) and fetal bovine serum (FBS, 3%) (GIBCO, all conc. final). Assay was performed under sterile conditions; only test compound preparation was non-sterile. Initial stock solutions were made in DMSO followed by dilution into RPMI 1640 2-fold higher than the desired final assay concentration. Confluent THP.1 cells ($2\times10^6$ cells/ml, final conc.; American Type Culture Company, Rockville, Md.) were added to 96 well polypropylene round bottomed culture plates (Costar 3790; sterile) containing 125 µl test compound (2 fold concentrated) or DMSO vehicle (controls, blanks). DMSO concentration did not exceed 0.2% final. Cell mixture was allowed to preincubate for 30 min, 37° C., 5% $CO_2$ prior to stimulation with lipopolysaccharide (LPS; 1 µg/ml final; Siga L-2630, from *E. coli* serotype 0111.B4; stored as 1 mg/ml stock in endotoxin screened distilled $H_2O$ at -80° C.). Blanks (unstimulated) received $H_2O$ vehicle; final incubation volume was 250 µl. Overnight incubation (18-24 hr) proceeded as described above. Assay was terminated by centrifuging plates 5 min, room temperature, 1600 rpm (400×g); supernatants were transferred to clean 96 well plates and stored -80° C. until analyzed for human TNFα by a commercially available ELISA kit (Biosource #KHC3015, Camarillo, Calif.). Data was analyzed by non-linear regression (Hill equation) to generate a dose response curve using SAS Software System (SAS institute, Inc., Cary, N.C.). The calculated $IC_{50}$ value is the concentration of the test compound that caused a 50% decrease in the maximal TNFα production.

In Vivo Assessment of MAPKAP-k2 Inhbitors:

B10.RIII mice were obtained from Jackson laboratories, LPS from Sigma Chemical Co. (# L-2880), D-+-galactosamine from Sigma chemical Co. (# G-0500) and Aerrane (isoflurane, USP) from Baxter Pharmaceuticals, NDC 10019-773-40. Animals were weighed and their tails were marked. Mice were anesthetized with isoflurane and their tails were warmed with gauze dipped in hot water prior to challenge. They were challenged with 200 ng of LPS/1 mg galactosamine in 200 uL per mouse delivered intravenously (i.v.) into the tail vein. 1 hour after challenge, the mice were anesthetized with isoflurane and were bled by cardiac punction. Approximately 100 uL were collected. The blood was dispensed into eppendorf tubes treated with EDTA and shaken. This procedure was repeated for all animals. The blood was centrifuged for ~5 minutes at 14,000 rpm in an eppendorf microfuge. The plasma was collected, put into labeled eppendorf tubes and frozen at -20° C. Plasma samples were then assayed for the presence of TNF-alpha using a mouse TNF-alpha ELISA duoset (DY410) kit purchased form R&D systems conducted as per the protocol supplied. Plasma samples are diluted to allow samples to fall on the linear portion of the standard response curve.

Methods of Using the Compounds of the Present Invention

In accordance with the invention, there are provided novel methods of using the compounds of the formula (I). The compounds disclosed therein effectively block inflammatory cytokine production from cells. The inhibition of cytokine production is an attractive means for preventing and treating a variety of cytokine mediated diseases or conditions associated with excess cytokine production, e.g., diseases and pathological conditions involving inflammation. Thus, the compounds are useful for the treatment of diseases and conditions as described in the Background section, including the following conditions and diseases: osteoarthritis, atherosclerosis, contact dermatitis, bone resorption diseases, reperfusion injury, asthma, multiple sclerosis, Guillain-Barre syndrome, Crohn's disease, ulcerative colitis, psoriasis, graft versus host disease, systemic lupus erythematosus and insulin-dependent diabetes mellitus, rheumatoid arthritis, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure. The compounds of the invention may also be useful for anti-coagulant or fibrinolytic therapy (and the diseases or conditions related to such therapy).

The compounds of the invention will be useful for treating oncological diseases and other cytokine mediated diseases and conditions related to p38 and MK2 as known in the art. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. The above described compounds may be physically combined with the conventional therapeutics or other adjuvants into a single pharmaceutical composition. Reference is this regard may be made to Cappola et al.: U.S. Pat. No. 6,565,880, PCT/US 01/21860 and U.S. application Ser. No. 10/214,782, each incorporated by reference herein in their entirety. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the compounds described herein include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. Reference in this regard may also be made to US publication No. US 2003-0118575 A1. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

We claim:

1. A compound of formula Ia:

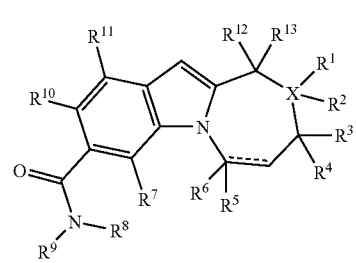

wherein:
the dashed line in the compound of formula I represents an optional double bond;
X is N
$R^1$ is hydrogen, hydroxy, carbamoyl, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{3-7}$ cycloalkyl, or $C_{1-6}$alkylthio $C_{1-6}$alkyl, wherein the sulfur atom, when present, is optionally oxidized to a sulfoxide or sulfone;
$R^2$ is optionally present and, if present, is hydrogen, hydroxy, ureido, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, $C_{3-7}$ cycloalkyl, or $C_{1-6}$ alkylthio, wherein the sulfur atom, when present, is optionally oxidized to a sulfoxide or sulfone;

$R^3$ is hydrogen, amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, carbamoyl, $CO_2C_{1-6}$alkyl, or $C_{1-6}$ alkylthio wherein the sulfur atom is optionally oxidized to a sulfoxide or sulfone; wherein each alkyl, amino, cycloalkyl, alkenyl, alkoxy, alkenyloxy, alkynyloxy, carbamoyl, and alkylthio group is optionally substituted by $R^x$ wherein $R^x$ can be chosen from:

hydrogen, amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, cyano, heteroaryl, $C_{3-7}$ cycloalkyl-$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, carbamoyl, ureido, —$CO_2C_{1-6}$alkyl or $C_{2-6}$ alkylthio wherein the sulfur atom is optionally oxidized to a sulfoxide or sulfone;

$R^4$ is optionally present and, when present, is hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, carbamoyl, or $C_{1-6}$ alkylthio wherein the sulfur atom is optionally oxidized to a sulfoxide or sulfone; wherein each alkyl, amino, cycloalkyl, alkenyl, alkoxy, alkenyloxy, alkynyloxy, carbamoyl, and alkylthio group is optionally substituted by $R^z$, and wherein $R^z$ can be chosen from:

amino, $C_{1-6}$ alkyl, $C_{2-6}$ alkenyl, amino $C_{1-6}$ alkyl, hydroxy$C_{1-6}$ alkyl, cyano $C_{1-6}$ alkyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, carbamoyl, ureido, or $C_{2-6}$ alkylthio wherein the sulfur atom is optionally oxidized to a sulfoxide or sulfone;

or $R^3$ and $R^4$ taken together represent oxo;

$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$ alkyl, di$C_{1-6}$alkylamino$C_{1-6}$alkyl, hydroxy, $C_{3-7}$ cycloalkyl, heterocyclyl, heterocyclyl$C_{1-6}$alkyl, aryl, aryloxy, acyl, heteroaryl, or $C_{1-6}$ alkylthio, wherein the sulfur atom is optionally oxidized to a sulfoxide or sulfone, and wherein each alkyl, cycloalkyl, alkenyl, aryl is optionally substituted by $R^x$, which is defined hereinabove, or =N—OH, =N—NHheteroaryl;

$R^6$ is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, or $C_{1-6}$ alkylthio, wherein the sulfur atom is optionally oxidized to a sulfoxide or sulfone, and wherein each alkyl, cycloalkyl, alkenyl, aryl is optionally substituted with single or multiple $R^x$, which is defined hereinabove, or $R^5$ and $R^6$, along with their substituents, may optionally be taken together to form a $C_{3-7}$ cycloalkyl that may be optionally substituted with single or multiple $R^x$, which is defined hereinabove;

$R^7$ is selected from hydrogen, $C_{1-6}$ alkyl, $C_{3-7}$ cycloalkyl, $C_{1-6}$ alkoxy, $C_{1-6}$alkoxy$C_{1-6}$ alkyl, hydroxy, hydroxy $C_{1-6}$ alkyl or amino optionally mono- or di-substituted by $C_{1-6}$ alkyl, aryl or aryl $C_{1-6}$ alkyl, or $R^7$ may be halo, haloalkyl, alkoxy, carboxyl, carbamoyl, nitro, dialkylamino, benzyloxy, hydrazinocarbonyl, alkoxycarbonyl, or alkoxycarbonylheterocyclylcarbonyl; wherein each alkyl, cycloalkyl, or aryl is optionally substituted with single or multiple $R^x$, which is defined hereinabove, $R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;

$R^9$ is chosen from hydrogen, halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl, aryloxy, acyl, heteroaryl, $C_{3-7}$ cycloalkyl-$C_{1-6}$ alkyl, aryl-$C_{1-6}$ alkyl, aryl-$C_{1-6}$ haloalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl or $C_{2-6}$ alkylthio, wherein the sulfur atom is optionally oxidized to a sulfoxide or sulfone; wherein each aryl, heterocycle or heteroaryl may be singly or multiply substituted with $R^y$, wherein $R^y$ may be chosen from:

halogen, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, heterocyclyl, aryl optionally substituted with $R^x$, aryloxy, acyl, heteroaryl optionally substituted with $R^x$, $C_{3-7}$ cycloalkyl-$C_{1-6}$ alkyl, aryl-$C_{1-6}$ alkyl, aryl-$C_{1-6}$ haloalkyl, aryl-$C_{1-6}$aminoalkyl, heterocyclyl-$C_{1-6}$ alkyl, heteroaryl-$C_{1-6}$ alkyl, $C_{3-7}$ cycloalkyl-$C_{2-6}$ alkenyl, aryl-$C_{2-6}$ alkenyl, heterocyclyl-$C_{2-6}$ alkenyl, heteroaryl-$C_{2-6}$ alkenyl, $C_{2-6}$ alkylthio wherein the sulfur atom is optionally oxidized to a sulfoxide or sulfone, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$, —C(O)N($R^a$)($R^b$) where $R^a$ and $R^b$ are independently selected from H, $C_{1-3}$alkyl, —$CH_2C(O)NH_2$, —$(CH_2)_n$OH, —$(CH_2)_n$NR$^c$R$^d$, where n=2 or 3 and $R^c$ and $R^d$ are independently selected from H, $C_{1-3}$alkyl and $C(O)CH_3$, or —C(O)NH—N=CH—R$^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —$CO_2C_{1-3}$alkyl, —$C(O)NH_2$, —OH, $C_{1-3}$alkyl, amino, $C_{1-3}$alkylamino and di$C_{1-3}$ alkylamino; or $R^8$ and $R^9$ can be taken together to form a heterocycloalkyl or heteroaryl ring, with the proviso that it can not be morpholine;

$R^{10}$ and $R^{11}$ are independently selected from hydrogen, $C_{1-6}$ alkoxy, hydroxy, halo, $C_{1-6}$ alkyl, $C_{3-7}$ cycloalkyl;

$R^{12}$ is selected from =S, oxo, $C_{1-6}$ alkyl, cyano, aminoalkyl, amino, haloalkyl, hydroxyalkyl, =N—O$R^z$, =N—N($R^z$)$_2$, wherein $R^T$ is selected from hydrogen or $C_{1-6}$ alkyl, $R^{13}$ is optionally present and, if present, is selected from hydrogen, $C_{1-6}$ alkyl, or a halo group or the pharmaceutically acceptable salts thereof.

2. The compound according to claim 1 wherein:

$R^1$ is hydrogen;

$R^2$ is optionally present and, if present, is hydrogen;

$R^3$ is hydrogen, $C_{1-6}$ alkyl, amino $C_{1-6}$ alkyl, hydroxy$C_{1-6}$ alkyl, cyano $C_{1-6}$ alkyl, $C_{3-7}$ cycloalkyl, carbamoyl or $CO_2C_{1-6}$alkyl; wherein each alkyl, cycloalkyl or carbamoyl group is optionally substituted by $R^x$ wherein $R^x$ can be chosen from:

hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbamoyl, or —$CO_2C_{1-6}$alkyl;

$R^4$ is optionally present and, when present, is hydrogen or $C_{1-6}$alkyl;

$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$alkyl, di$C_{1-6}$alkylamino$C_{1-6}$alkyl, hydroxy, heterocyclyl$C_{1-6}$alkyl, wherein the heterocyclyl is chosen from pyrrolidinyl, piperidinyl, piperazinyl, and morpholinyl, $C_{3-7}$ cycloalkyl, acyl, =N—OH or =N—NHheteroaryl;

$R^6$ is hydrogen or $C_{1-6}$ alkyl, optionally partially or fully halogenated, or $R^5$ and $R^6$, may optionally be taken together to form a $C_{3-7}$ cycloalkyl;

$R^7$ is hydrogen, hydroxyl or $C_{1-6}$ alkoxy;

$R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;

$R^9$ is chosen from hydrogen, $C_{1-6}$ alkyl, piperidinyl, phenyl and heteroaryl, wherein each phenyl, piperidinyl or heteroaryl may be singly or multiply substituted with $R^y$, wherein $R^y$ may be chosen from:

halogen, $C_{1-6}$ alkyl, $C_{2-6}$ alkenyl, $C_{1-6}$ alkoxy, hydroxy, $C_{3-7}$ cycloalkyl, phenyl, phenoxy, acyl, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$, —C(O)N($R^a$)($R^b$) where $R^a$ and $R^b$ are independently selected from H, $C_{1-3}$alkyl, —$CH_2C(O)NH_2$, —$(CH_2)_nOH$ and —$(CH_2)_nNR^cR^d$, where n=2 or 3 and $R^c$ and $R^d$ are independently selected from H, $C_{1-3}$alkyl and C(O)$CH_3$, or —C(O)NH—N=CH—$R^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —$CO_2C_{1-3}$alkyl, —C(O)$NH_2$, —OH, $C_{1-3}$alkyl, amino, $C_{1-3}$alkylamino and di$C_{1-3}$alkylamino;

$R^{10}$ and $R^{11}$ are hydrogen;

$R^{12}$ is selected from =S, oxo, $C_{1-6}$ alkyl, cyano, aminoalkyl, amino, haloalkyl, hydroxyalkyl, =N—$OR^z$, =N—N($R^z$)$_2$, wherein $R^z$ is selected from hydrogen or $C_{1-6}$ alkyl; and $R^{13}$ is optionally present and, if present, is selected from hydrogen, $C_{1-6}$ alkyl, or a halo group.

3. The compound according to claim 2 wherein:

$R^1$ is hydrogen;

$R^2$ is optionally present and, if present, is hydrogen;

$R^3$ is hydrogen, $C_{1-6}$ alkyl, amino $C_{1-6}$ alkyl, hydroxy$C_{1-6}$ alkyl, cyano $C_{1-6}$ alkyl, $C_{3-7}$ cycloalkyl, carbamoyl or $CO_2C_{1-6}$alkyl; wherein each alkyl, cycloalkyl or carbamoyl group is optionally substituted by $R^x$ wherein $R^x$ can be chosen from:

hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkenyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbamoyl, or —$CO_2C_{1-6}$alkyl;

$R^4$ is optionally present and, when present, is hydrogen or $C_{1-6}$alkyl;

$R^5$ is optionally present and, when present, is hydrogen, oxo, $C_{1-6}$ alkyl, optionally partially or fully halogenated, $C_{2-6}$ alkenyl, $C_{2-6}$ alkynyl, $C_{1-6}$ alkoxy, $C_{2-6}$ alkenyloxy, $C_{2-6}$ alkynyloxy, amino$C_{1-6}$alkyl, $C_{1-6}$alkylamino$C_{1-6}$alkyl, di$C_{1-6}$alkylamino$C_{1-6}$alkyl, hydroxy, heterocyclyl$C_{1-6}$alkyl, wherein the heterocyclyl is chosen from pyrrolidinyl, piperidinyl, piperazinyl, and morpholinyl, $C_{3-7}$ cycloalkyl, acyl, =N—OH or =N—NHheteroaryl;

$R^6$ is hydrogen or $C_{1-6}$ alkyl, optionally partially or fully halogenated, or $R^5$ and $R^6$, may optionally be taken together to form a $C_{3-7}$ cycloalkyl;

$R^7$ is hydrogen, hydroxyl, or $C_{1-6}$ alkoxy;

$R^8$ is chosen from hydrogen, $C_{1-6}$ alkyl, $C_{2-6}$ alkenyl, $C_{2-6}$ alkynyl, $C_{1-6}$ alkoxy, or $C_{3-7}$ cycloalkyl;

$R^9$ is chosen from hydrogen, $C_{1-6}$alkyl, piperidinyl, phenyl, heteroaryl selected from pyridyl, quinolinyl, thiazolyl, indolyl, benzothiazolyl, benzoxazolyl, isoxazolyl, pyrazinyl, pyrimidinyl, benzimidazolyl, oxazolyl, pyrazolyl, 1,3,4-thiadiazolyl, tetrazolyl, 1,3,4-oxadiazolyl, 1,2,4-triazolyl, imidazolyl, pyrrolyl, thiophene, benzothiophene, furanyl and benzofuran wherein each phenyl, piperidinyl or heteroaryl may be singly or multiply substituted with $R^y$, wherein $R^y$ may be chosen from:

halogen, $C_{1-6}$ alkyl, $C_{2-6}$ alkenyl, $C_{1-6}$ alkoxy, hydroxy, $C_{3-7}$ cycloalkyl, phenyl, phenoxy, acyl, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$, —C(O)N($R^a$)($R^b$) where $R^a$ and $R^b$ are independently selected from H, $C_{1-3}$alkyl, —$CH_2C(O)NH_2$, —$(CH_2)_nOH$ and —$(CH_2)_nNR^cR^d$, where n=2 or 3 and $R^c$ and $R^d$ are independently selected from H, $C_{1-3}$alkyl and C(O)$CH_3$, or , —C(O)NH—N=CH—$R^e$, where $R^e$ is aryl or heteroaryl optionally substituted with $R^x$, or $R^a$ and $R^b$ together with the N they are connected to can form a pyrrolidine, piperazine, piperidine or morpholine ring optionally substituted with one to three groups selected from —$CO_2C_{1-3}$alkyl, —C(O)$NH_2$, —OH, $C_{1-3}$alkyl, amino, $C_{1-3}$alkylamino and di$C_{1-3}$alkylamino;

$R^{10}$ and $R^{11}$ are hydrogen;

$R^{12}$ is selected from =S, oxo, $C_{1-6}$ alkyl, cyano, aminoalkyl, amino, haloalkyl, hydroxyalkyl, =N—$OR^z$, =N—N($R^z$)$_2$, wherein $R^z$ is selected from hydrogen or $C_{1-6}$ alkyl; and $R^{13}$ is optionally present and, if present, is selected from hydrogen, $C_{1-6}$ alkyl, or a halo group.

4. The compound according to claim 3 wherein:

$R^1$ is hydrogen;

$R^3$ is hydrogen, $C_{1-6}$ alkyl, amino $C_{1-6}$ alkyl, hydroxy$C_{1-6}$ alkyl, cyano $C_{1-6}$ alkyl, $C_{3-7}$ cycloalkyl, carbamoyl or $CO_2C_{1-6}$alkyl; wherein each alkyl, cycloalkyl or carbamoyl group is optionally substituted by $R^x$ wherein $R^x$ can be chosen from:

hydrogen, amino, $C_{1-6}$ alkyl, $C_{2-6}$ alkenyl, amino $C_{1-6}$ alkyl, hydroxy $C_{1-6}$ alkyl, cyano $C_{1-6}$ alkyl, $C_{2-6}$ alkynyl, $C_{1-6}$ alkoxy, $C_{2-6}$ alkenyloxy, $C_{2-6}$ alkynyloxy, hydroxy, $C_{3-7}$ cycloalkyl, acyl, $C_{3-7}$ cycloalkyl-$C_{1-6}$ alkyl, $C_{3-7}$ cycloalkyl-$C_{2-6}$ alkenyl, carbamoyl, or —$CO_2C_{1-6}$alkyl;

$R^4$ is optionally present and, when present, is selected from hydrogen, or $C_{1-6}$alkyl;

$R^5$ is optionally present and, when present, is hydrogen, $C_{1-6}$ alkyl or $CF_3$;

$R^6$ is hydrogen, $C_{1-6}$ alkyl or $CF_3$; or $R^5$ and $R^6$, may optionally be taken together to form a $C_{3-7}$ cycloalkyl;

$R^7$ is hydrogen;

$R^8$ is hydrogen;

$R^9$ is chosen from hydrogen, $C_{1-6}$ alkyl, piperidinyl, phenyl, heteroaryl selected from pyridyl, quinolinyl, thiazolyl, indolyl, benzothiazolyl, benzoxazolyl, isoxazolyl, pyrazinyl, pyrimidinyl, benzimidazolyl, oxazolyl, pyrazolyl, 1,3,4-thiadiazolyl, tetrazolyl, 1,3,4-oxadiazolyl, 1,2,4-triazolyl, imidazolyl, pyrrolyl, thiophene, benzothiophene, furanyl and benzofuran, wherein each phenyl, piperidinyl or heteroaryl may be singly or multiply substituted with $R^y$, wherein $R^y$ may be chosen from:

halogen, $C_{1-6}$ alkyl, $C_{2-6}$ alkenyl, $C_{1-6}$ alkoxy, hydroxy, $C_{3-7}$ cycloalkyl, phenyl, phenoxy, acyl, —$OCF_3$, amino, $C_{1-3}$alkylamino, di$C_{1-3}$alkylamino, acylamino, hydroxyethylamino, —CN, —$CO_2C_{1-3}$alkyl, —$CH_2NH_2$ or —$C(O)N(R^a)(R^b)$ where $R^a$ and $R^b$ are independently selected from H, $C_{1-3}$alkyl, —$CH_2C(O)NH_2$, —$(CH_2)_n OH$ and —$(CH_2)_n NR^c R^d$, where n=2 or 3 and $R^c$ and $R^d$ are independently selected from H, $C_{1-3}$alkyl and $C(O)CH_3$, and —$C(O)NH$—N=CH—$R^e$, where $R^e$ is phenyl, or $R^a$ and $R^b$ together with the N they are connected to can form a pyrrolidine, piperazine, piperidine or morpholine ring optionally substituted with one to three groups selected from —$CO_2C_{1-3}$alkyl, —$C(O)NH_2$, —OH, $C_{1-3}$alkyl, amino, $C_{1-3}$alkylamino and di$C_{1-3}$alkylamino;

$R^{10}$ and $R^{11}$ are hydrogen; and $R^{12}$ is oxo.

5. A pharmaceutical composition comprising a pharmaceutically effective amount of a compound according to claim 1 and one or more pharmaceutically acceptable carriers and/or adjuvants.

\* \* \* \* \*